(12) United States Patent
Boykin et al.

(10) Patent No.: US 7,256,203 B2
(45) Date of Patent: Aug. 14, 2007

(54) DICATIONIC 2,5-DIARYLFURAN AZA-ANALOGS AS ANTI-PROTOZOAN AGENTS

(75) Inventors: David W. Boykin, Atlanta, GA (US); Richard R. Tidwell, Pittsboro, NC (US); Mohamed A. Ismail, Mansoura (EG); Reto Brun, Basel (CH)

(73) Assignees: The University of North Carolina at Chapel Hill, Chapel Hill, NC (US); Georgia State University Research Foundation, Inc., Atlanta, GA (US)

( * ) Notice: Subject to any disclaimer, the term of this patent is extended or adjusted under 35 U.S.C. 154(b) by 381 days.

(21) Appl. No.: 10/721,525

(22) Filed: Nov. 25, 2003

(65) Prior Publication Data

US 2004/0122015 A1 Jun. 24, 2004

Related U.S. Application Data

(60) Provisional application No. 60/429,717, filed on Nov. 27, 2002.

(51) Int. Cl.
*A61K 31/44* (2006.01)
*C07D 401/02* (2006.01)

(52) U.S. Cl. .................. 514/336; 514/461; 546/281.7; 546/276.4; 546/280.4; 549/429

(58) Field of Classification Search ............. 546/281.7, 546/276.4, 280.4; 549/429; 514/336, 461
See application file for complete search history.

(56) References Cited

U.S. PATENT DOCUMENTS 6,706,754 B2    3/2004 Werbovetz et al.

FOREIGN PATENT DOCUMENTS

WO    WO 00/04893 A2 *    2/2000
WO    WO 01/03685 A2 *    1/2001
WO    WO02/36588          5/2002

OTHER PUBLICATIONS

Ismail, M. A. et al., "Synthesis and Antiprotozoal Activity of Aza-Analogues of Furamidine", *Journal of Medicinal Chemistry*, vol. 46, No. 22, pp. 4761-4769, 2003.
Trent, J. O. et al., Targeting the Minor Groove of DNA: Crystal Structures of Two Complexes Between Furan Derivatives of Berenil and the DNA Dodecamer d(CGCGAATTCGCG)$_2$, *Journal of Medicinal Chemistry*, vol. 39, No. 23, pp. 4554-4562, 1996.
International Preliminary Examination Report corresponding PCT Appl. No. PCT/US03/37691 dated Jul. 6, 2004.
Bell et al., Structure-Activity Relationships of Analogs of Pentamidine Against Plasmodium falciparum and Leishmania mexicana amazonensis, Antimicrobial Agents and Chemotherapy 34(7):1381-1386 (Jul. 1990).
Bell et al., Structure-Activity Relationships of Pentamidine Analogs against Giardia lamblia and Correlation of Antigiardial Activity with DNA-Binding Affinity, Antimicrobial Agents and Chemotherapy 35(6):1099-1107 (Jun. 1991).
Blagburn et al., Inhibition of Cryptosporidium parvum in Neonatal Hsd:(ICR)BR Swiss Mice by Polyether Ionophores and Aromatic Amidines, Antimicrobial Agents and Chemotherapy 35(7):1520-1523 (Jul. 1991).
Boykin et al., Dicationic Diarylfurans and Anti-pneumocystis carinii Agents, J. Med. Chem. 38:912-916 (1995).
Boykin et al., 2,5-Bis[4-(N-alkylamidino)phenyl]furans as Anti-pneumocystis carinii Agents, J. Med. Chem. 41:124-129 (1998).
Das et al., Synthesis and Antiprotozoal Activity of 2,5-Bis(4-guanylphenyl)furans, J. of Med. Chem. 20(4):531-536 (1977).
Del Poeta et al., Structure-in Vitro Activity Relationships of Pentamidine Analogues and Dication-Substituted Bis-Benzimidazoles as New Antifungal Agents, Antimicrobial Agents and Chemotherapy 42(10):2495-2502 (Oct. 1998).
Del Poeta et al., In Vitro Antifungal Activities of a Series of Dication-Substituted Cabazoles, Furans, and Benzimidazoles, Antimicrobial Agents and Chemotherapy 42(10):2503-2510 (Oct. 1998).
Del Poeta et al., In-vitro activity of dicationic aromatic compounds and fluconazole against Cryptococcus neoformans and Candida ssp, J. of Antimicrobial Chemotherapy 44:223-228 (1999).
Francesconi et al., 2,4-Diphenyl Furan Diamidines as Novel Anti-Pneumocystis carnii Pneumonia Agents, J. Med. Chem. 42:2260-2265 (1999).
Kumar et al., Palladium Catalyzed Cross-Coupling Reactions for the Synthesis of 2.5-disubstitutedfurans, Hetercyclic Comm. 5:301-304 (1999).
Lindsay et al., Activity of Pentamidine and Pentamidine Analogs against Toxoplasma gondii in Cell Cultures, Antimicrobial Agents and Chemotherapy 35(9):1914-1916 (Sep. 1991).
Ling et al., Models for Intramolecular Exchange in Organic π-Conjugated Open-Shell Systems: 3-Nitrenophenyl and 4-Nitrenophenyl Units Connected by 2,5-Furandiyl, 2,5-Thiophenediyl, and 2,5-Pyrrolediyl Nonalternant Exchange Linkers, J. Am. Chem. Soc. 116:8784-8792 (1994).
Shearer et al., S-2-Naphthylmethyl Thioacetimidate Hydrobromide: A New Odorless Reagent for the Mild Synthesis of Substituted Acetamidines, Tetrahedron Lett. 38:179-182 (1997).
Stephens, et al., Diguanidino and "Reversed" Diamindino 2,5-Diarylfurans asn Antimicrobial Agents, J. Med. Chem 44:1741-1748 (2001).
Thompson et al., A General Synthesis of 5-Arylnicotinates, J. Org. Chem. 49:5237-5243 (1984).

* cited by examiner

*Primary Examiner*—Zinna N. Davis
(74) *Attorney, Agent, or Firm*—Jenkins, Wilson, Taylor & Hunt, P.A.

(57) ABSTRACT

A compound of Formula (I):

(1)

$R^{14}-D^1\begin{matrix}R^8\\|\\C^1\end{matrix}\underset{\underset{L^1}{\overset{\|}{B}}}{\overset{A}{=}}\begin{matrix}R^{15}\;\;\;R^{16}\\\diagdown\;\;/\\\diagup\;\;\diagdown\\X\end{matrix}\underset{\underset{L^2}{\overset{\|}{Y}}}{\overset{}{}}\begin{matrix}R^1\\|\\C^2\end{matrix}-R^{13}$

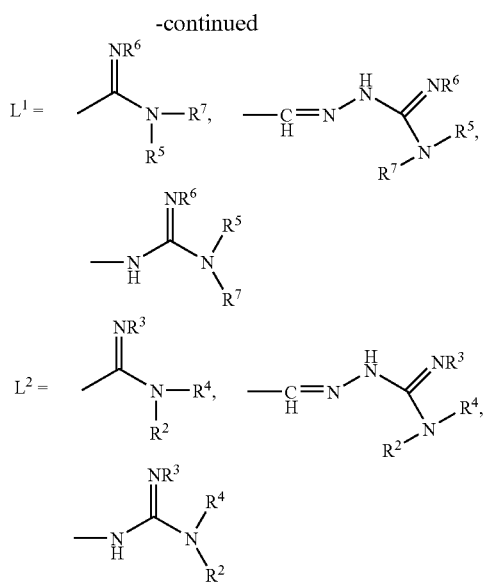

wherein:
X is selected from the group consisting of O, S, and $NR^{17}$, where $R^{17}$ is hydrogen or lower alkyl;
A and Y are CH, N, $NR^{17}$, O, or S;
$C^1$ and $C^2$ are each C or N, wherein $C^1$ and $C^2$ are the same or different;
$D^1$ and $D^2$ are each C or N, wherein $D^1$ and $D^2$ are the same or different;
B and Z are CH, N, or $NR^{17}$, provided that B, Z, or both B and Z are not present when A, Y, or both A and Y are O, S, or $NR^{17}$;

$R^{13}$, $R^{14}$, $R^1$ and $R^8$ can be present or absent, and when present are selected from the group consisting of H, lower alkyl, halogen, alkoxyl, aryloxyl, aralkoxy and hydroxyl;

$R^{15}$ and R are selected from the group consisting of H, lower alkyl, halogen, alkoxyl, aryloxyl, aralkoxy and hydroxyl;

$R^3$ and $R^6$ are each independently selected from the group consisting of H, hydroxy, lower alkyl, cycloalkyl, aryl, aralkyl, alkoxyl, hydroxycycloalkyl, alkoxycycloalkyl, hydroxyalkyl, aminoalkyl, acyloxy, acetoxy, and alkylaminoalkyl; and $R^2$, $R^4$, $R^5$ and $R^7$ are each independently selected from the group consisting of H, lower alkyl, alkoxyalkyl, cycloalkyl, aryl, aralkyl, hydroxyalkyl, aminoalkyl, and alkylaminoalkyl, or $R^2$ and $R^4$ together or $R^5$ and $R^7$ together represent a $C_2$ to $C_{10}$ alkyl, hydroxyalkyl, or alkylene, or $R^3$ and $R^4$ together or $R^6$ and $R^7$ together are:

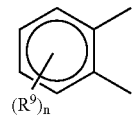

wherein n is a number from 1 to 3, and $R^9$ is H or —$CONHR^{10}NR^{11}R^{12}$, wherein $R^{10}$ is lower alkyl and $R^{11}$ and $R^{12}$ are each independently selected from the group consisting of H and lower alkyl.

15 Claims, No Drawings

DICATIONIC 2,5-DIARYLFURAN AZA-ANALOGS AS ANTI-PROTOZOAN AGENTS

RELATED APPLICATIONS

This application claims the benefit of U.S. Provisional Patent Application Ser. No. 60/429,717, filed Nov. 27, 2002; the disclosure of which is incorporated herein by reference in its entirety.

FIELD OF THE INVENTION

The present invention relates to methods of combating microbial infections with dicationic compounds. More particularly, the present invention relates to methods of combating microbial infections with heteroaryl diamidine prodrugs and to the novel heteroaryl diamidine prodrugs themselves.

BACKGROUND ART

The incidence of microbial infections (e.g., mycobacterial, fungal and protozoal infections) in the immunocompromised population has significantly increased over the past several years. In particular, *Candida* species, especially *Candida albicans*, are often significant pathogens in patients infected with human immunodeficiency virus (HIV). Another pathogen, *Pneumocystis carinii*, causes a form of pneumonia (PCP) that is believed to be one of the leading causes of death in patients suffering from AIDS.

Human African trypanosomiasis (HAT) has reemerged as a threat to over 60 million people. Current estimates are that between 350,000 and 450,000 people are infected.

Other severe and life-threatening microbial infections are caused by *Mycobacterium tuberculosis, Aspergillus* spp., *Cryptosporidium parvum, Giardia lamblia, Plasmodium* spp., *Toxoplasma gondii, Fusarium solani*, and *Cryptococcus neoformans*.

The antimicrobial properties of dicationic molecules have been studied since the 1930's. Compounds of this type have typically utilized amidine groups as the cationic moieties, and their activities against a number of pathogens including *Cryptosporidium parvum, Giardia lamblia, Leishmania* spp., *Plasmodium* spp., *Pneumocystis carinii, Toxoplasma gondii, Trypanosoma* spp., *Candida albicans, Aspergillus* spp. and *Cryptococcus neoformans* have been reported. See e.g., King, H. et al., *Ann. Trop. Med. Parasitol.* 1938, 32, 177–192; Blagburn, B. L. et al., *Antimicrob. Agents Chemother.* 1991, 35, 1520–1523; Bell, C. A. et al., *Antimicrob. Agents Chemother.* 1991, 35, 1099–1107; Bell, et al., *Antimicrob. Agents Chemother.* 1990, 34, 1381–1386; Kirk, R. et al., *Ann. Trop. Med. Parastiol.* 1940, 34,181–197; Fulton, J. D. *Ann. Trop. Med. Parasitol.* 1940, 34, 53–66; Ivady, V. G. et al., *Monatschr. Kinderheilkd.* 1958, 106, 10–14; Boykin, D. W. et al., *J. Med. Chem.* 1995, 38, 912–916; Boykin, D. W. et al., *J. Med. Chem.* 1998, 41, 124–129; Francesconi et al., *J. Med. Chem.* 1999, 42, 2260–2265; Lindsay, D. S. et al., *Antimicrob. Agents Chemother.* 1991, 35, 1914–1916; Lourie, E. M. et al., *Ann. Trop. Med. Parasitol.* 1939, 33, 289–304; Lourie, E. M. et al., *Ann. Trop. Med. Parasitol.* 1939, 33, 305–312; Das, B. P. et al., *J Med. Chem.* 1976, 20, 531–536; Del Poeta, M. et al., *J. Antimicrob. Chemother.* 1999, 44, 223–228; Del Poeta, M. et al., *Antimicrob. Agents Chemother.* 1998, 42, 2495–2502; Del Poeta, M. et al., *Antimicrob. Agents Chemother.* 1998, 42, 2503–2510.

Despite the broad range of activity exhibited by diamidines, only one compound of this chemical type, pentamidine, has seen significant clinical use. Pentamidine has been used clinically against African trypanosomiasis, antimony-resistant leishmaniasis and *P. carinii* pneumonia. See e.g., Apted, F. I. C., *Pharmacol. Ther.* 1980, 11, 391–413; Bryceson, A. D. M. et al., *Trans. Roy. Soc. Trop. Med. Hyg.* 1985, 79, 705–714; Hughes, W. T. et al., *Antimicrob. Agents Chemother.* 1974, 5, 289–293.

Thus, there continues to be a need for improvement in the art for additional compounds having desirable anti-microbial activity, whether against the representative pathogens referenced above or against other pathogens. Of particular interest would be a compound having activity in the treatment of human African trypanosomiasis, an infectious disease having no currently available oral treatment in its second stage. This present invention addresses this and other needs in the art.

SUMMARY OF THE INVENTION

Accordingly, a first aspect of the present invention is a compound of Formula (I);

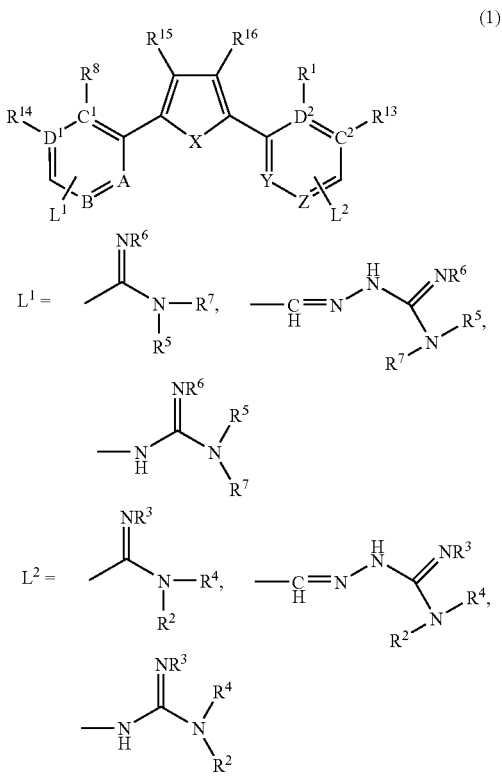

wherein:
X is selected from the group consisting of O, S, and $NR^{17}$, where $R^{17}$ is hydrogen or lower alkyl;
A and Y are CH, N, $NR^{17}$, O, or S;
$C^1$ and $C^2$ are each C or N, wherein $C^1$ and $C^2$ are the same or different;
$D^1$ and $D^2$ are each C or N, wherein $D^1$ and $D^2$ are the same or different;
B and Z are CH, N, or $NR^{17}$, provided that B, Z, or both B and Z are not present when A, Y, or both A and Y are O, S, or $NR^{17}$;

$R^{13}$, $R^{14}$, $R^1$ and $R^8$ can be present or absent, and when present are selected from the group consisting of H, lower alkyl, halogen, alkoxyl, aryloxyl, aralkoxy and hydroxyl;

$R^{15}$ and $R^{16}$ are selected from the group consisting of H, lower alkyl, halogen, alkoxyl, aryloxyl, aralkoxyl and hydroxyl;

$R^3$ and $R^6$ are each independently selected from the group consisting of H, hydroxy, lower alkyl, cycloalkyl, aryl, aralkyl, alkoxyl, hydroxycycloalkyl, alkoxycycloalkyl, hydroxyalkyl, aminoalkyl, acyloxy, acetoxy, and alkylaminoalkyl; and $R^2$, $R^4$, $R^5$ and $R^7$ are each independently selected from the group consisting of H, lower alkyl, alkoxyalkyl, cycloalkyl, aryl, aralkyl, hydroxyalkyl, aminoalkyl, and alkylaminoalkyl, or $R^2$ and $R^4$ together or $R^5$ and $R^7$ together represent a $C_2$ to $C_{10}$ alkyl, hydroxyalkyl, or alkylene, or $R^3$ and $R^4$ together or $R^6$ and $R^7$ together are:

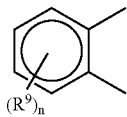

wherein n is a number from 1 to 3, and $R^9$ is H or —CONHR$^{10}$NR$^{11}$R$^{12}$, wherein $R^{10}$ is lower alkyl and $R^{11}$ and $R^{12}$ are each independently selected from the group consisting of H and lower alkyl.

A second aspect of the present invention is a method of treating microbial infection comprising administering an effective amount of a compound of Formula I to a subject in need thereof.

A third aspect of the invention is a pharmaceutical formulation comprising a compound of Formula I in a pharmaceutically acceptable carrier.

Another aspect of the present invention includes the use of an active compound as described above for the preparation of a medicament for treating a microbial infection.

Several aspects and objects of the invention having been stated hereinabove, and which are addressed in whole or in part by the present invention, other aspects and objects will become evident as the description proceeds when taken in connection with the accompanying Examples as best described herein below.

DETAILED DESCRIPTION OF THE INVENTION

The present invention will be now be described more fully hereinafter with reference to the accompanying Examples, in which preferred embodiments of the invention are shown. This invention can, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

Throughout the specification and claims, a given chemical formula or name shall encompass all optical and stereoisomers as well as racemic mixtures where such isomers and mixtures exist.

Disclosed herein is a compound of the Formula (I):

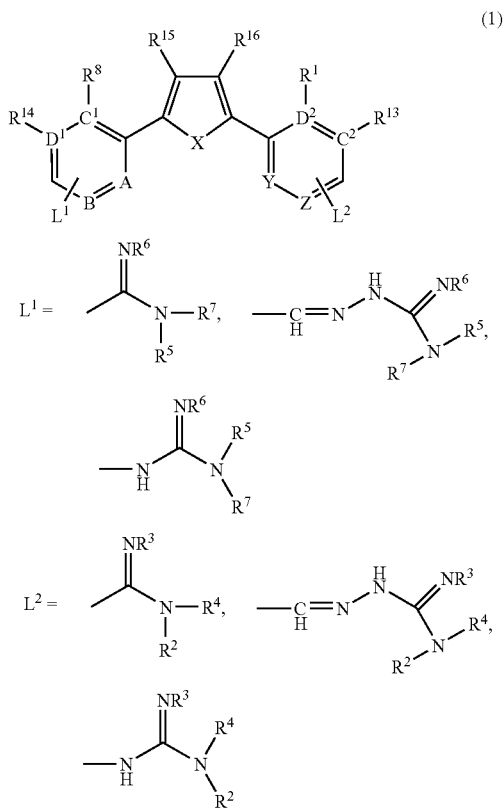

wherein:

X is selected from the group consisting of O, S, and NR$^{17}$, where R$^{17}$ is hydrogen or lower alkyl;

A and Y are CH, N, NR$^{17}$, O, or S;

$C^1$ and $C^2$ are each C or N, wherein $C^1$ and $C^2$ are the same or different;

$D^1$ and $D^2$ are each C or N, wherein $D^1$ and $D^2$ are the same or different;

B and Z are CH, N or NR$^{17}$, provided that B, Z, or both B and Z are not present when A, Y, or both A and Y are O, S, or NR$^{17}$;

$R^{13}$, $R^{14}$, $R^1$ and $R^8$ can be present or absent, and when present are selected from the group consisting of H, lower alkyl, halogen, alkoxyl, aryloxyl, aralkoxy and hydroxyl;

$R^{15}$ and $R^{16}$ are selected from the group consisting of H, lower alkyl, halogen, alkoxyl, aryloxyl, aralkoxy and hydroxyl;

$R^3$ and $R^6$ are each independently selected from the group consisting of H, hydroxy, lower alkyl, cycloalkyl, aryl, aralkyl, alkoxyl, hydroxycycloalkyl, alkoxycycloalkyl, hydroxyalkyl, aminoalkyl, acyloxy, acetoxy, and alkylaminoalkyl; and $R^2$, $R^4$, $R^5$ and $R^7$ are each independently selected from the group consisting of H, lower alkyl, alkoxyalkyl, cycloalkyl, aryl, aralkyl, hydroxyalkyl, aminoalkyl, and alkylaminoalkyl, or $R^2$ and $R^4$ together or $R^5$ and $R^7$ together represent a $C_2$ to $C_{10}$ alkyl, hydroxyalkyl, or alkylene, or $R^3$ and $R^4$ together or $R^6$ and $R^7$ together are:

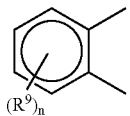

wherein n is a number from 1 to 3, and $R^9$ is H or —CONHR$^{10}$NR$^{11}$R$^{12}$, wherein $R^{10}$ is lower alkyl and $R^{11}$ and $R^{12}$ are each independently selected from the group consisting of H and lower alkyl.

As used herein the term "alkyl" refers to $C_{1-20}$ inclusive, linear, branched, or cyclic, saturated or unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Lower alkyl" refers to an alkyl group having 1 to about 8 carbon atoms, i.e. 1, 2, 3, 4, 5, 6, 7 or 8 carbon atoms. "Higher alkyl" refers to an alkyl group having about 10 to about 20 carbon atoms.

The alkyl group can be optionally substituted with one or more alkyl group substituents which can be the same or different, where "alkyl group substituent" includes alkyl, halo, arylamino, acyl, hydroxy, aryloxy, alkoxyl, alkylthio, arylthio, aralkyloxy, aralkylthio, carboxy, alkoxycarbonyl, oxo and cycloalkyl. There can be optionally inserted along the alkyl chain one or more oxygen, sulphur or substituted or unsubstituted nitrogen atoms, wherein the nitrogen substituent is hydrogen, lower alkyl (also referred to herein as "alkylaminoalkyl"), or aryl. "Branched" refers to an alkyl group in which a lower alkyl group, such as methyl, ethyl or propyl, is attached to a linear alkyl chain.

"Aryl" refers to a cyclic aromatic containing about 5 to about 10 carbon atoms, including 5 and 6-membered hydrocarbon and heterocyclic aromatic rings. The aryl group can be optionally substituted with one or more aryl group substituents which can be the same or different, where "aryl group substituent" includes alkyl, aryl, aralkyl, hydroxy, alkoxyl, aryloxy, aralkoxyl, carboxy, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene and —NRR', where R and R' can be each independently hydrogen, alkyl, aryl and aralkyl.

Specific examples of aryl groups include but are not limited to cyclopentadienyl, phenyl, furan, thiophene, pyrrole, pyran, pyridine, imidazole, isothiazole, isoxazole, pyrazole, pyrazine, pyrimidine, and the like.

Thus, as used herein, the terms "substituted alkyl" and "substituted aryl" include alkyl and aryl groups, as defined herein, in which one or more atoms or functional groups of the aryl or alkyl group are replaced with another atom or functional group, including for example, halogen, aryl, alkyl, alkoxyl, hydroxy, nitro, amino, alkylamino, dialkylamino, sulfate, and mercapto.

As used herein, the term "acyl" refers to an organic acid group wherein the —OH of the carboxyl group has been replaced with another substituent (i.e., as represented by RCO—, wherein R is an alkyl or an aryl group as defined herein). As such, the term "acyl" specifically includes arylacyl groups. Specific examples of acyl groups include acetyl and benzoyl.

"Cyclic" and "Cycloalkyl" refer to a non-aromatic mono- or multicyclic ring system of about 4 to about 10 carbon atoms. The cycloalkyl group can be optionally partially unsaturated. The cycloalkyl group can be also optionally substituted with an alkyl group substituent as defined herein, oxo and/or alkylene. There can be optionally inserted along the cyclic alkyl chain one or more oxygen, sulphur or substituted or unsubstituted nitrogen atoms, wherein the nitrogen substituent is hydrogen, lower alkyl, or aryl, thus providing a heterocyclic group. Representative monocyclic cycloalkyl rings include cyclopentyl, cyclohexyl and cycloheptyl. Preferred multicyclic cycloalkyl rings include adamantyl, octahydronaphthyl, decalin, camphor, camphane, and noradamantyl.

"Alkoxyl" refers to an alkyl-O— group wherein alkyl is as previously described. The term "alkoxyl" as used herein can refer to $C_{1-20}$ inclusive, linear, branched, or cyclic, saturated or unsaturated oxo-hydrocarbon chains, including for example methoxy, ethoxy, propoxy, isopropoxy, butoxy, t-butoxy, and pentoxy.

"Aryloxyl" refers to an aryl-O— group wherein the aryl group is as previously described. The term "aryloxyl" as used herein can refer to phenyloxyl or hexyloxyl, and alkyl, halo, or alkoxyl substituted phenyloxyl or hexyloxyl.

"Aralkyl" refers to an aryl-alkyl- group wherein aryl and alkyl are as previously described. Exemplary aralkyl groups include benzyl, phenylethyl and naphthylmethyl.

"Aralkyloxyl" refers to an aralkyl-O— group wherein the aralkyl group is as previously described. An exemplary aralkyloxy group is benzyloxy.

"Dialkylamino" refers to an —NRR' group wherein each of R and R' is independently an alkyl group as previously described. Exemplary alkylamino groups include ethylmethylamino, dimethylamino and diethylamino.

"Alkoxycarbonyl" refers to an alkyl-O—CO— group. Exemplary alkoxycarbonyl groups include methoxycarbonyl, ethoxycarbonyl, butyloxycarbonyl and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an $H_2N$—CO— group.

"Alkylcarbamoyl" refers to a R'RN—CO— group wherein one of R and R' is hydrogen and the other of R and R' is alkyl as previously described.

"Dialkylcarbamoyl" refers to R'RN—CO— group wherein each of R and R' is independently alkyl as previously described.

"Acyloxyl" refers to an acyl-O— group wherein acyl is as previously described.

"Acylamino" refers to an acyl-NH— group wherein acyl is as previously described.

"Aroylamino" refers to an aroyl-NH— group wherein aroyl is as previously described.

"Alkylene" refers to a straight or branched bivalent aliphatic hydrocarbon group having from 1 to about 20 carbon atoms. The alkylene group can be straight, branched or cyclic. The alkylene group can be also optionally unsaturated and/or substituted with one or more "alkyl group substituents." There can be optionally inserted along the alkylene group one or more oxygen, sulphur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—);

—CH=CH—CH=CH—; —CH=CH—CH$_2$—; —(CH$_2$)$_n$—N(R)—(CH$_2$)$_m$—, wherein each of m and n is independently an integer from 0 to about 20 and R is hydrogen or lower alkyl; methylenedioxy (—O—CH$_2$—O—); and ethylenedioxy (—O—(CH$_2$)$_2$—O—). An alkylene group can have about 2 to about 3 carbon atoms and can further have 6–20 carbons.

The terms "halo", "halide", or "halogen" as used herein refer to fluoro, chloro, bromo, and iodo groups.

In a particular embodiment, the present invention comprises a compound having the formula (II):

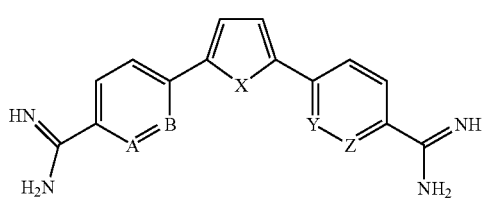

A, B, Y, Z = CH or N
X = O or S

In a particular embodiment, the present invention comprises a compound having the formula (III):

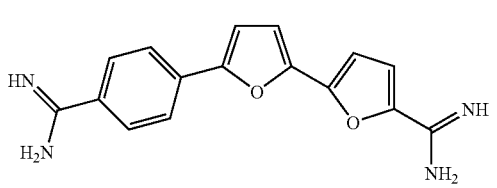

In representative embodiments, several disymmetric heteroaryl diamidines have been synthesized. For example, 6-[5-(4-carbamimidoylphenyl)furan-2-yl]nicotinamidine has been synthesized from 6-[5-(4-cyanophenyl)furan-2-yl]nicotinonitrile, through the bis-O-acetoxyamidoxime followed by hydrogenation. 6-[5-(4-cyanophenyl)furan-2-yl]nicotinonitrile has been prepared via bromination of 6-(furan-2-yl)nicotinonitrile, followed by Suzuki coupling with 4-cyanophenylboronic acid. 6-[5-(4-cyano-2-methylphenyl)furan-2-yl]nicotinonitrile has been prepared from 6-(furan-2-yl)nicotinonitrile by a Heck coupling reaction with 4-bromo-3-methylbenzonitrile.

In representative embodiments, compounds disclosed herein are prodrugs. A prodrug means a compound that, upon administration to a recipient, is capable of providing (directly or indirectly) a compound of this invention or an inhibitorily active metabolite or residue thereof. Prodrugs can increase the bioavailability of the compounds of this invention when such compounds are administered to a subject (e.g., by allowing an orally administered compound to be more readily absorbed into the blood) or can enhance delivery of the parent compound to a biological compartment (e.g., the brain or lymphatic system) relative to a metabolite species, for example. A number of the compounds (e.g. compounds 4, 5, 11, 12, 22 and 27) discussed in Examples 1–8 are prodrugs.

Additionally, the active compounds can be administered as pharmaceutically acceptable salts. Such salts include the gluconate, lactate, acetate, tartarate, citrate, phosphate, borate, nitrate, sulfate, and hydrochloride salts. The salts of the present invention can be prepared, in general, by reacting two equivalents of the base compound with the desired acid, in solution. After the reaction is complete, the salts are crystallized from solution by the addition of an appropriate amount of solvent in which the salt is insoluble.

Subjects with microbial infections can be treated by the methods of the present invention. These infections can be caused by a variety of microbes, including fungi, algae, protozoa, bacteria, and viruses. Exemplary microbial infections that can be treated by the method of the present invention include, but are not limited to, infections caused by *Trypanosoma* species (e.g. *Trypanosoma brucei rhodesiense*), *Pnemocytsis carnii*, *Giardia lamblia*, *Cryptosporidium parvum*, *Cryptococcus neoformans*, *Candida albicans*, *Candida tropicalis*, *Salmonella typhimurium*, *Plasmodium falciparum*, *Leishmania donovani*, and *Leishmania mexicana amazonensis*. The methods of the invention are useful for treating these conditions in that they inhibit the onset, growth, or spread of the condition, cause regression of the condition, cure the condition, or otherwise improve the general well-being of a subject afflicted with, or at risk of contracting the condition.

The subject treated in the present invention in its many embodiments is desirably a human subject, although it is to be understood that the principles of the invention indicate that the invention is effective with respect to all vertebrate species, which are intended to be included in the term "subject".

The methods of the present invention are particularly useful in the treatment and/or prevention of infectious diseases in warm-blooded vertebrates. Thus, the invention concerns mammals and birds.

More particularly, provided is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, contemplated is the treatment of livestock, including, but not limited to, domesticated swine (pigs and hogs), ruminants, horses, poultry, and the like.

As noted above, the present invention provides pharmaceutical formulations comprising the aforementioned active compounds, or pharmaceutically acceptable salts thereof, in pharmaceutically acceptable carriers for oral, intravenous, or aerosol administration as discussed in greater detail below. Also, the present invention provides such compounds or salts thereof which have been lyophilized and which can be reconstituted to form pharmaceutically acceptable formulations for administration, as by intravenous or intramuscular injection.

The therapeutically effective dosage of any specific compound, the use of which is in the scope of present invention, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 10 mg/kg to about 50 mg/kg may be employed for oral administration. Typically, a dosage from about 0.5 mg/kg to 5 mg/kg may be employed for intramuscular injection. Preferred dosages are 1 µmol/kg to 50 µmol/kg, and more preferably 22 µmol/kg and 33 µmol/kg of the compound for intravenous or oral administration. The duration of the treatment is usually once per day for a period of two to three weeks or until the condition is essentially controlled. Lower doses given less frequently can be used prophylactically to prevent or reduce the incidence of recurrence of the infection.

In accordance with the present method, pharmaceutically active compounds as described herein, or pharmaceutically acceptable salts thereof, can be administered orally as a solid or as a liquid, or can be administered intramuscularly or intravenously as a solution, suspension, or emulsion. Alternatively, the compounds or salts can also be administered by inhalation, intravenously or intramuscularly as a liposomal suspension. When administered through inhalation the active compound or salt should be in the form of a plurality of solid particles or droplets having a particle size from about 0.5 to about 5 microns, and preferably from about 1 to about 2 microns.

The present invention also provides a pharmaceutical composition suitable for intravenous or intramuscular injection. The pharmaceutical composition comprises a compound of any Formula (I)–(III) described herein, or a pharmaceutically acceptable salt thereof, in any pharmaceutically acceptable carrier. If a solution is desired, water is the carrier of choice with respect to water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and typically by filtration through a 0.22-micron filter. Subsequent to sterilization, the solution can be dispensed into appropriate receptacles, such as depyrogenated glass vials. Of course, the dispensing is preferably done by an aseptic method. Sterilized closures can then be placed on the vials and, if desired, the vial contents may be lyophilized.

In addition to compounds of Formulas (I)–(III) or their salts, the pharmaceutical compositions can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions can contain anti-microbial preservatives. Useful anti-microbial preservatives include methylparaben, propylparaben, and benzyl alcohol. The anti-microbial preservative is typically employed when the formulation is placed in a vial designed for multi-dose use. Of course, as indicated, the pharmaceutical compositions of the present invention can be lyophilized using techniques well known in the art.

In yet another aspect of the present invention, there is provided an injectable, stable, sterile composition comprising a compound of any one of Formulas (I)–(III), or a salt thereof, in a unit dosage form in a sealed container. The compound or salt is provided in the form of a lyophilizate, which is capable of being reconstituted with a suitable pharmaceutically acceptable carrier to form a liquid composition suitable for injection thereof into a subject. The unit dosage form typically comprises from about 10 mg to about 10 grams of the compound salt. When the compound or salt is substantially water-insoluble, a sufficient amount of emulsifying agent, which is physiologically acceptable, can be employed in sufficient quantity to emulsify the compound or salt in an aqueous carrier. One such useful emulsifying agent is phosphatidyl choline.

Other pharmaceutical compositions can be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same can be incorporated into lipid vesicles. In such an instance, due to the water solubility of the compound or salt, the compound or salt will be substantially entrained within the hydrophilic center or core of the liposomes. The lipid layer employed can be of any conventional composition and can either contain cholesterol or can be cholesterol-free. When the compound or salt of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques.

Of course, the liposomal formulations containing the compounds disclosed herein or salts thereof, can be lyophilized to produce a lyophilizate, which can be reconstituted with a pharmaceutically acceptable carrier, such as water, to regenerate a liposomal suspension.

Pharmaceutical formulations are also provided which are suitable for administration as an aerosol, by inhalation. These formulations comprise a solution or suspension of a desired compound described herein or a salt thereof, or a plurality of solid particles of the compound or salt. The desired formulation can be placed in a small chamber and nebulized. Nebulization can be accomplished by compressed air or by ultrasonic energy to form a plurality of liquid droplets or solid particles comprising the compounds or salts. The liquid droplets or solid particles should have a particle size in the range of about 0.5 to about 10 microns, more preferably from about 0.5 to about 5 microns. The solid particles can be obtained by processing the solid compound or a salt thereof, in any appropriate manner known in the art, such as by micronization. Most preferably, the size of the solid particles or droplets will be from about 1 to about 2 microns. In this respect, commercial nebulizers are available to achieve this purpose. The compounds can be administered via an aerosol suspension of respirable particles in a manner set forth in U.S. Pat. No. 5,628,984, the disclosure of which is incorporated herein by reference in its entirety.

Preferably, when the pharmaceutical formulation suitable for administration as an aerosol is in the form of a liquid, the formulation will comprise a water-soluble compound or a salt thereof, in a carrier that comprises water. A surfactant can be present, which lowers the surface tension of the formulation sufficiently to result in the formation of droplets within the desired size range when subjected to nebulization.

As indicated, the present invention provides both water-soluble and water-insoluble compounds and salts thereof. As used in the present specification, the term "water-soluble" is meant to define any composition that is soluble in water in an amount of about 50 mg/mL, or greater. Also, as used in the present specification, the term "water-insoluble" is meant to define any composition that has solubility in water of less than about 20 mg/mL. For certain applications, water-soluble compounds or salts can be desirable whereas for other applications water-insoluble compounds or salts likewise can be desirable.

EXAMPLES

The following Examples have been included to illustrate modes of the invention. Certain aspects of the following Examples are described in terms of techniques and procedures found or contemplated by the present co-inventors to work well in the practice of the invention. These Examples illustrate standard laboratory practices of the co-inventors. In light of the present disclosure and the general level of skill in the art, those of skill can appreciate that the following Examples are intended to be exemplary only and that numerous changes, modifications, and alterations can be employed without departing from the scope of the invention.

In the Examples, mM means millimolar, mL means milliliters, mm means millimeters, cm means centimeters, C means degrees Celsius, g means grams, kg means kilograms, m.p. means melting point, MHz means megahertz, M means molar, h means hours, NMR means nuclear magnetic resonance, FAB means fast atom bombardment, DMF means dimethylformamide, EtOH means ethyl alcohol, DMSO means dimethylsulfoxide, HPLC means high-pressure liquid chromatography, TLC means thin-layer chromatography, dec means decomposition point, NBS means N-bromosuccinimide; KO-t-Bu means potassium tert-butoxide; Bu means butyl; $NH_2OH.HCl$ means hydroxylamine hydrochloride; Me means methyl; MeO means methoxy; Ac means acetyl; AcO means acetoxy; AcOH means acetic acid; $Ac_2O$ means acetic anhydride; B means boron in schemes; Pd/C means 10% palladium on carbon; Hz meant hertz; δ means chemical shifting; TMS means trimethylsilyl; P. f. means *Plasmodium falciparum*; T. br. *Trypanosoma brucei rhodesiense*; L. d. means *Leishmania donovani*; MS means mass spectroscopy; calcd means calculated; EtOAc means ethyl acetate; THF means tetrahydrofuran; psi means pounds per square inch; UV means ultraviolet.

Example 1

Scheme 1

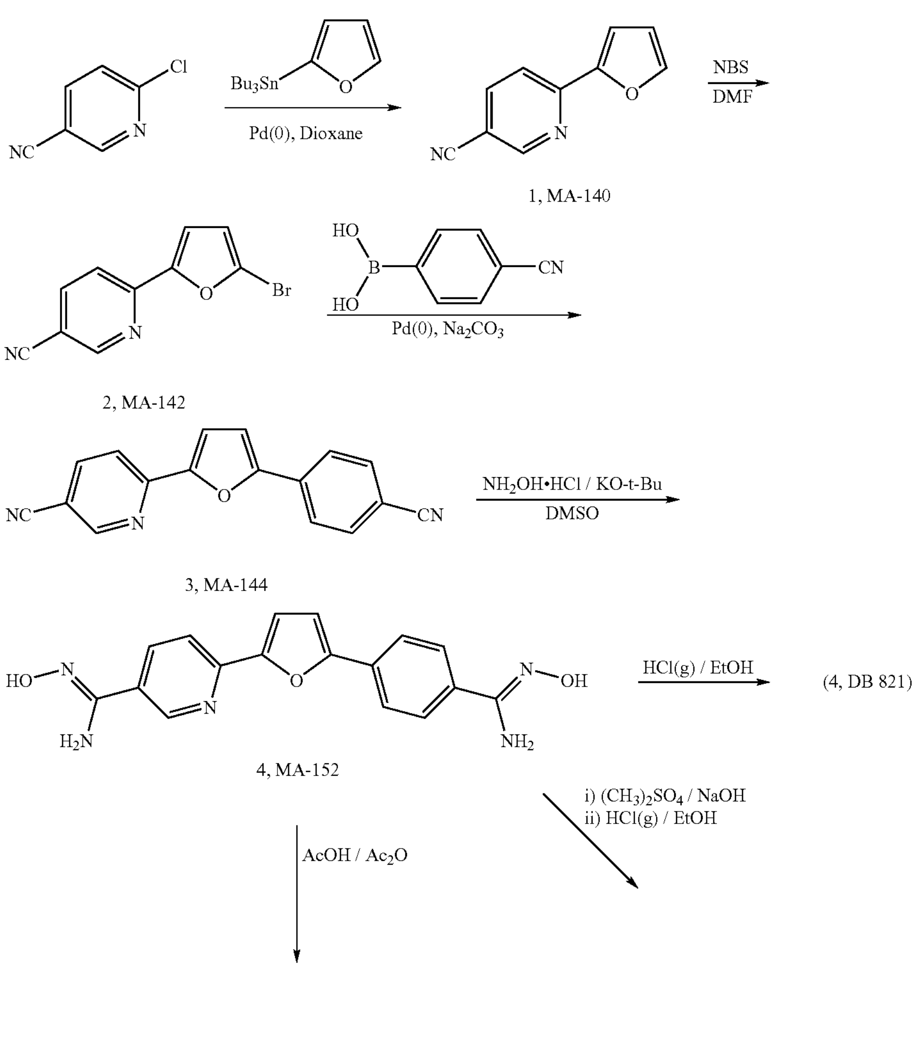

1, MA-140

2, MA-142

3, MA-144

4, MA-152

-continued
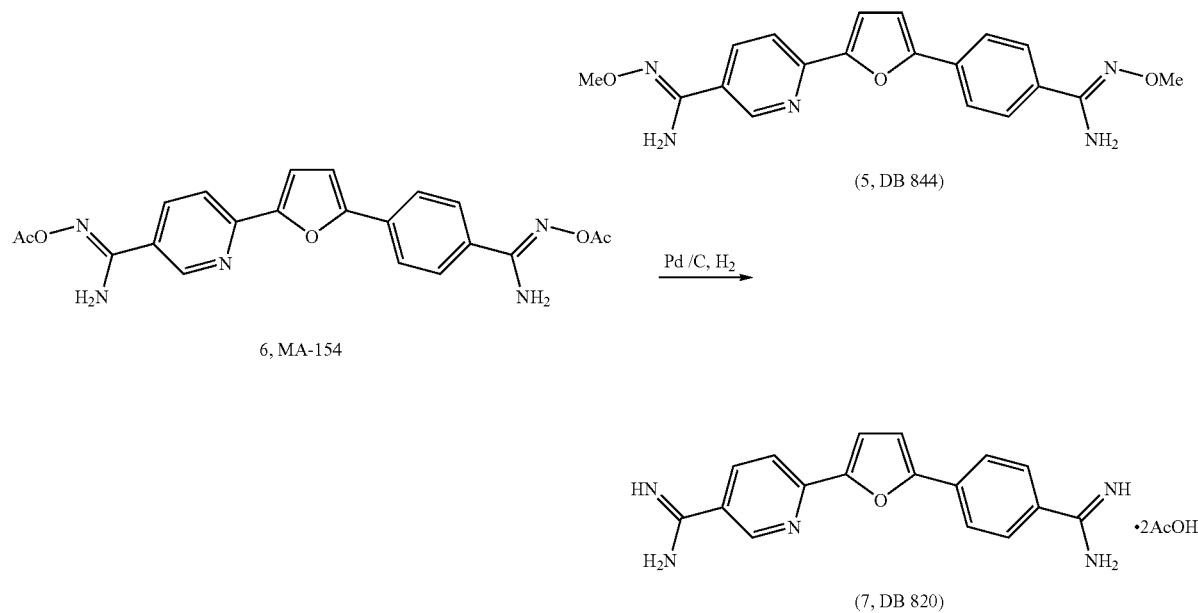
Example 2
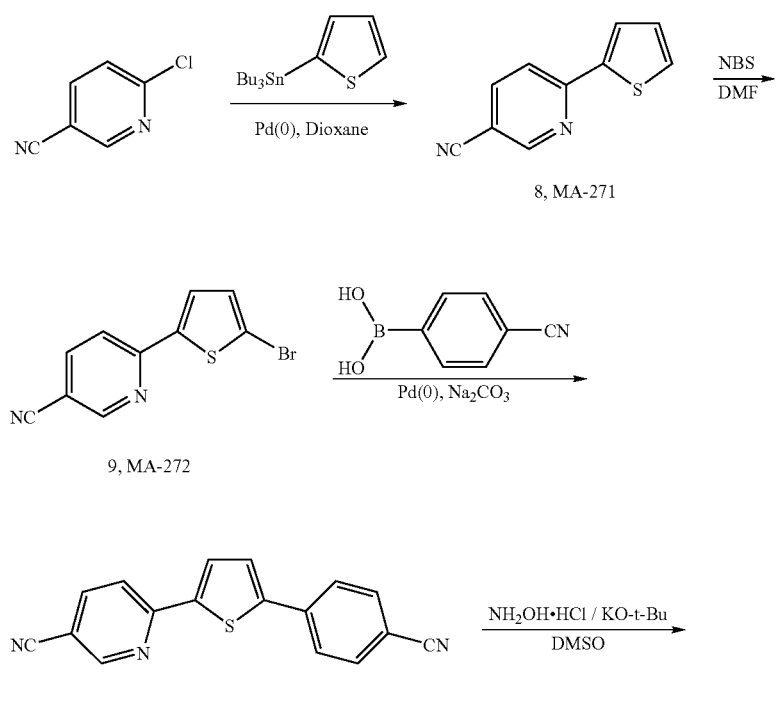

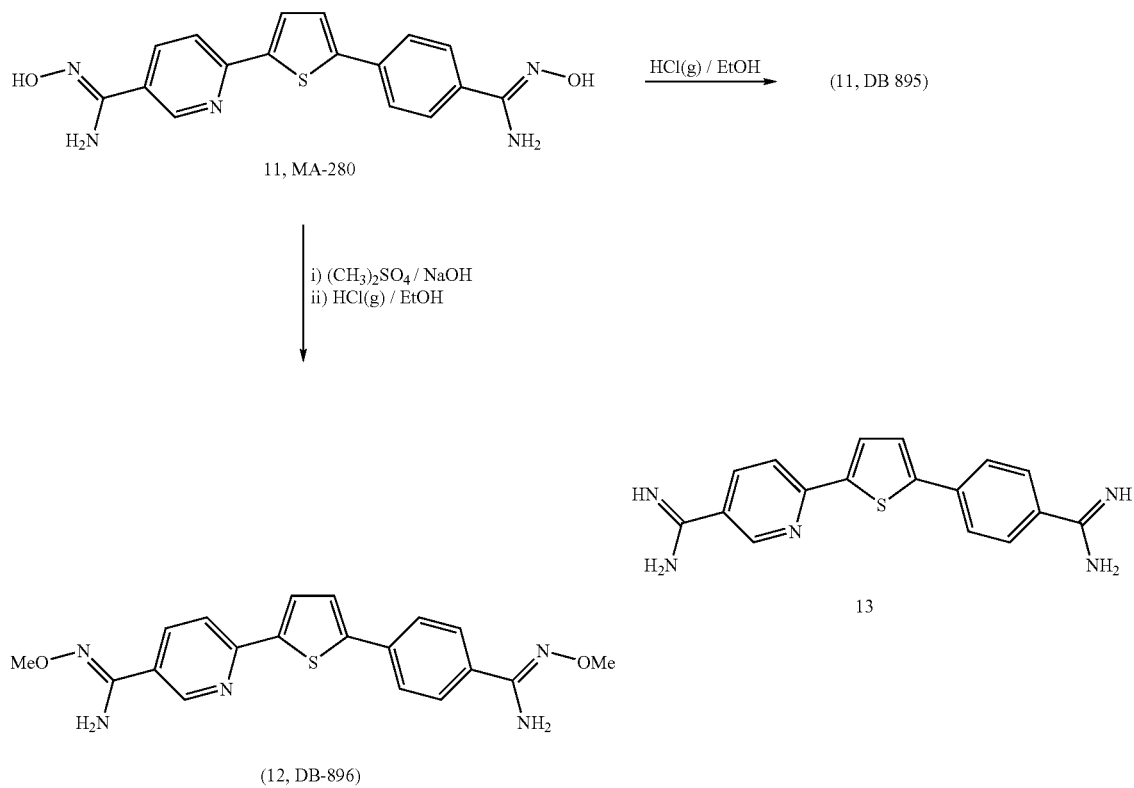
Example 3
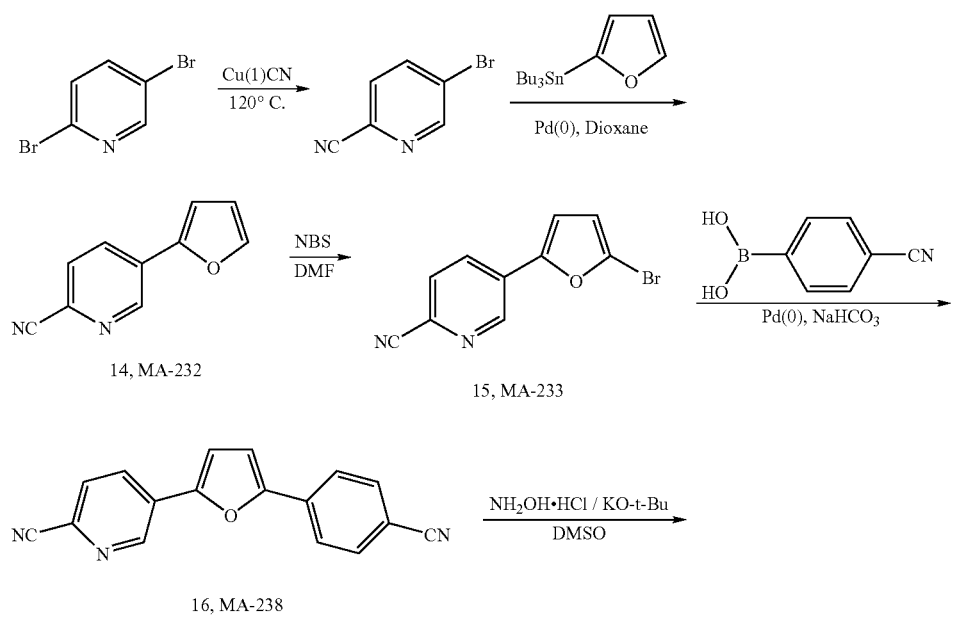

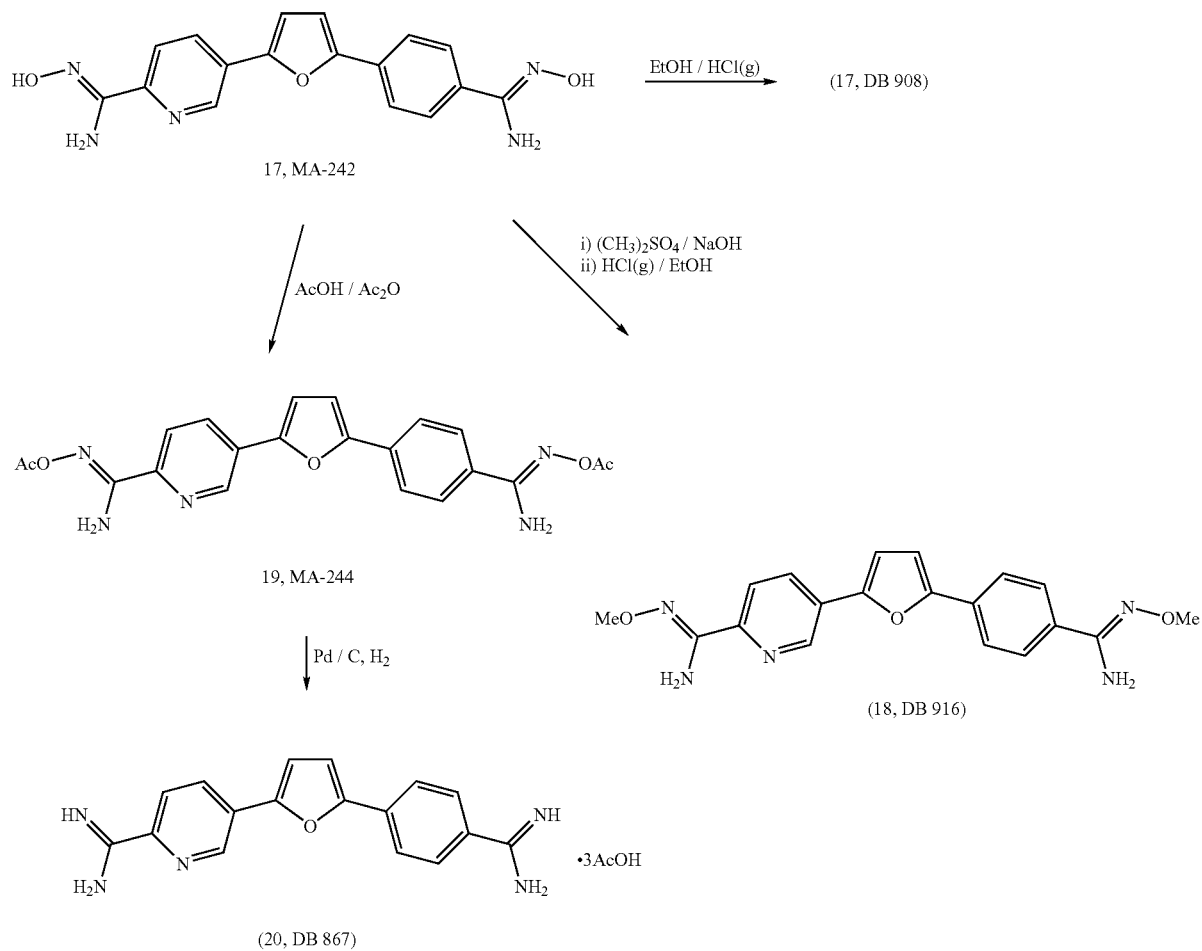
Example 4
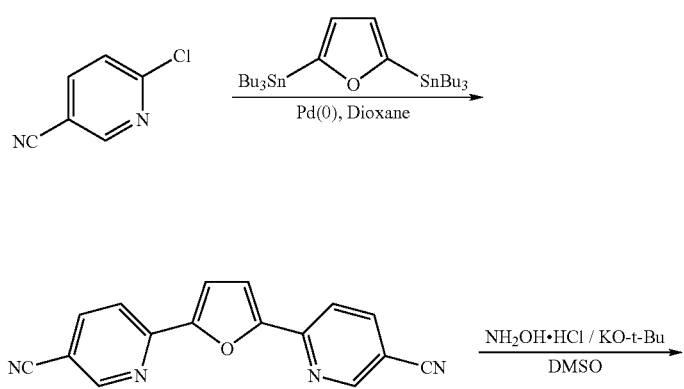

-continued
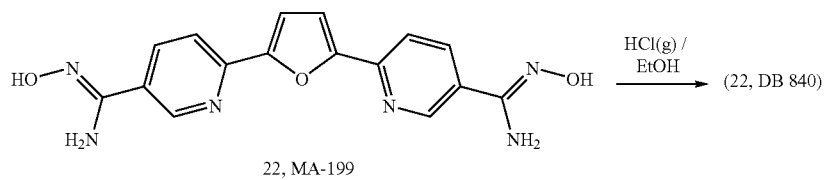
22, MA-199 → (22, DB 840)  
HCl(g) / EtOH
AcOH / Ac₂O ↓
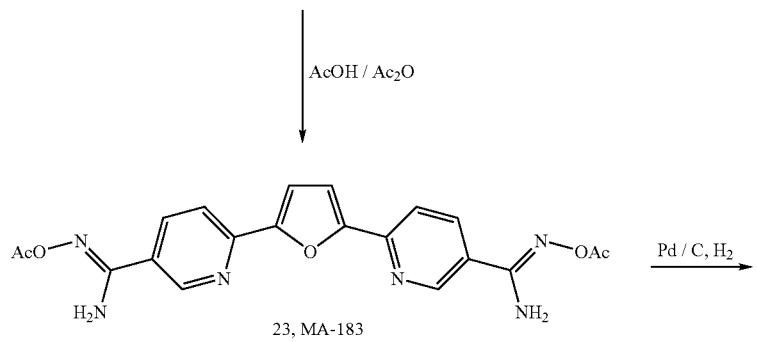
23, MA-183
Pd / C, H₂ →
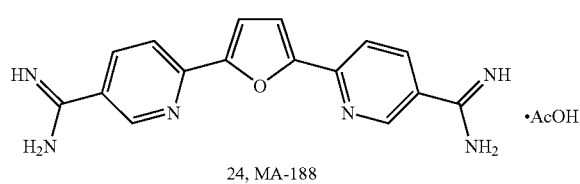
24, MA-188 · AcOH
1) 1 N NaOH
2) HCl (g) / EtOH ↓
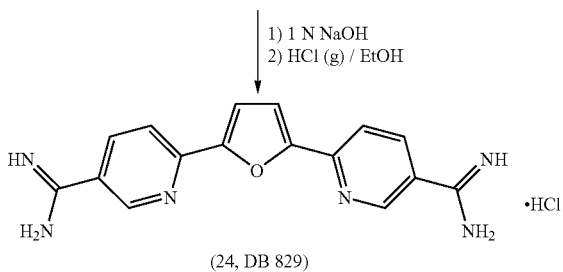
(24, DB 829) · HCl
Example 5
Scheme 5
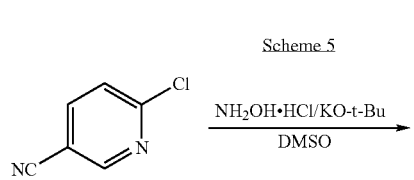
NH₂OH·HCl/KO-t-Bu
DMSO →
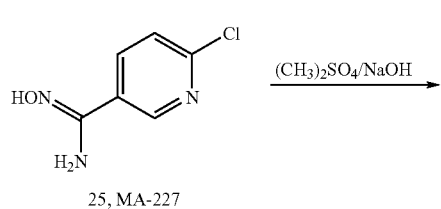
25, MA-227
(CH₃)₂SO₄/NaOH →
-continued
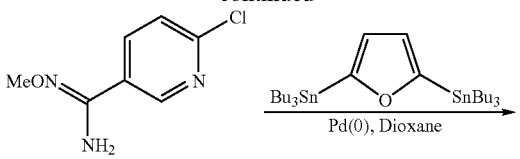
26, MA-228
Bu₃Sn—(furan)—SnBu₃
Pd(0), Dioxane →
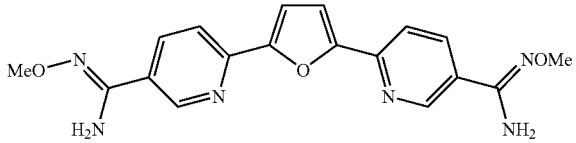
27, MA-234
HCl(g) / EtOH ↓
(27, DB 868)

Example 6
Scheme 6
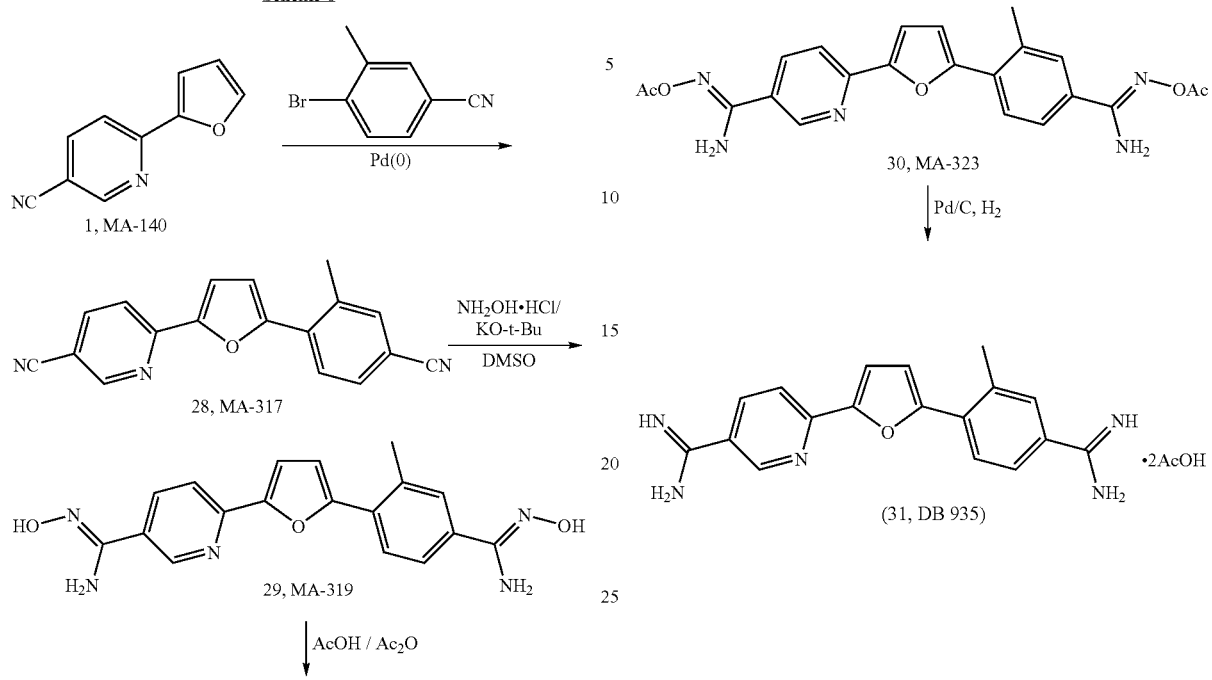
Example 7
Scheme 7
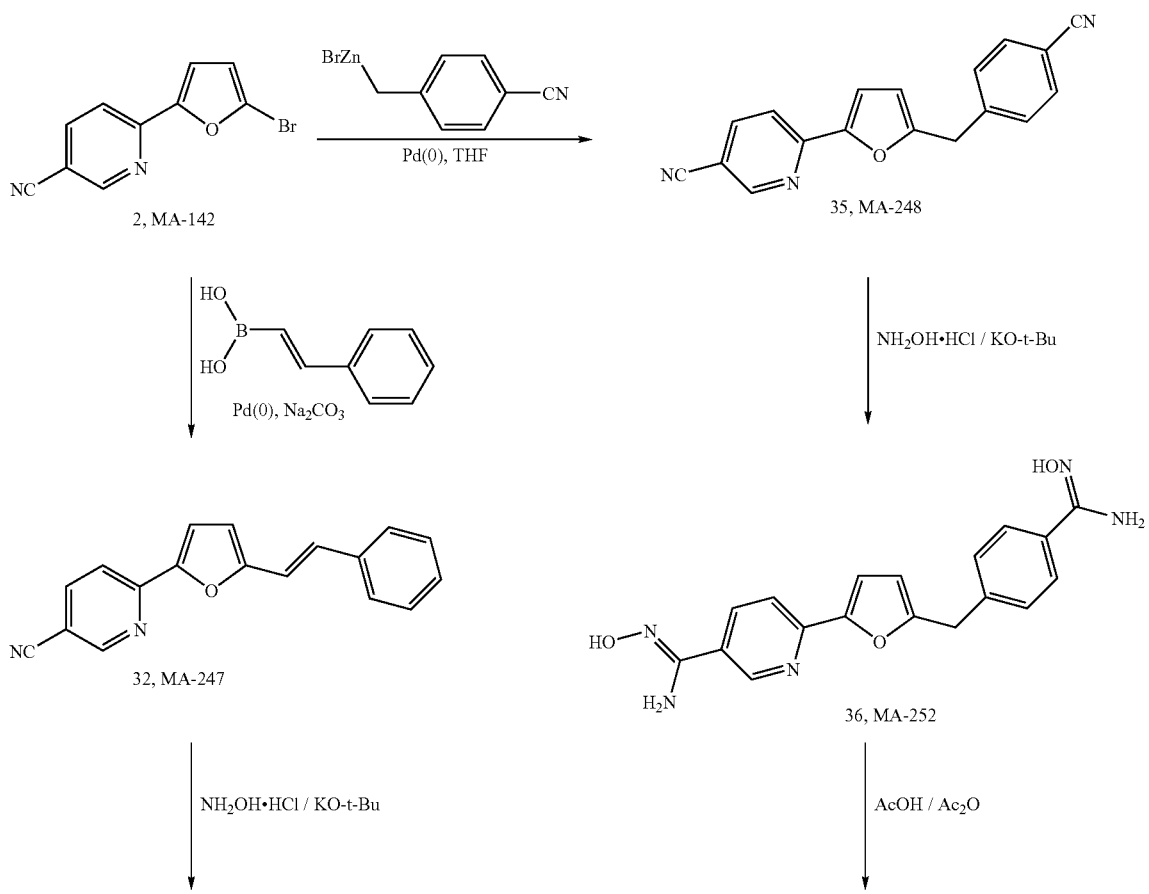

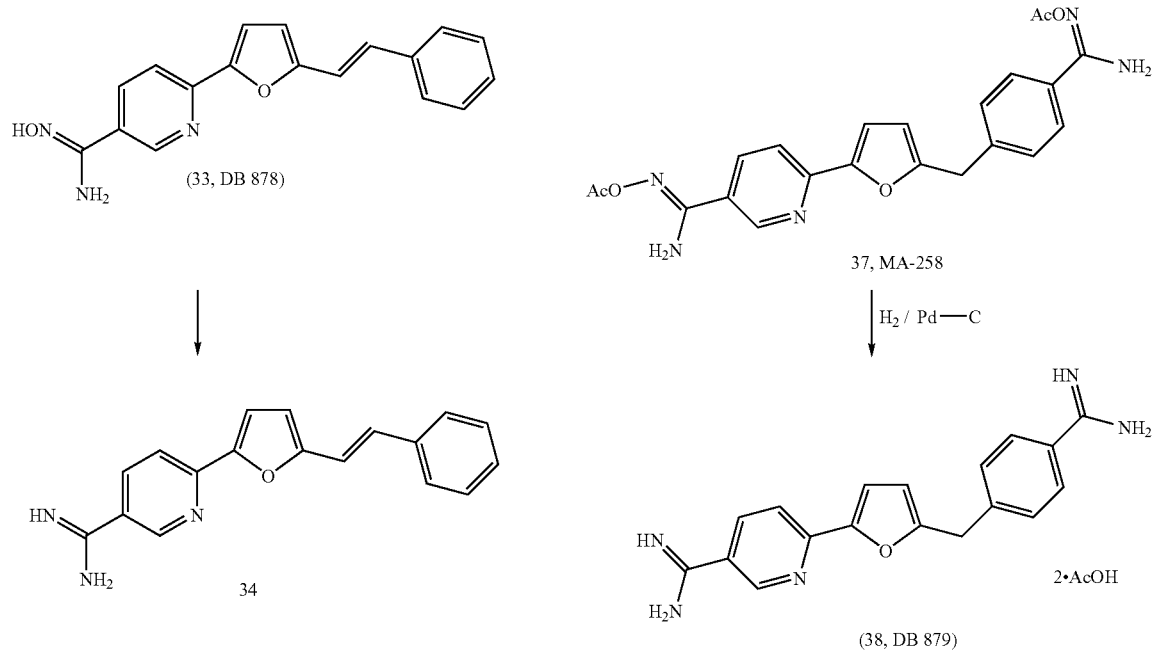

Experimental Section for Examples 1–7

Melting points were recorded using a THOMAS-HOOVER UNI-MELT™ capillary melting point apparatus and are uncorrected. TLC analysis was carried out on silica gel 60 $F_{254}$ precoated aluminum sheets and detected under UV light. $^1H$ and $^{13}C$ NMR spectra were recorded employing a Varian GX400 or Varian Unity Plus 300 spectrometer (available from Varian, Inc. of Palo Alto, Calif., United States of America), and chemical shifts (δ) are in ppm relative to TMS as internal standard. Mass spectra were recorded on a VG analytical 70-SE spectrometer (available from Varian, Inc. of Palo Alto, Calif., United States of America). Elemental analyses were obtained from Atlantic Microlab Inc. (Norcross, Ga., United States of America) and are within ±0.4 of the theoretical values. All chemicals and solvents were purchased from Aldrich Chemical Company, St. Louis, Mo., United States of America, or Fisher Scientific of Suwanee, Ga., United States of America.

6-(Furan-2-yl)nicotinonitrile (1). Referring now to Scheme 1, a mixture of 6-chloronicotinonitrile (4.155 g, 30 mmol), 2-tributyltin furan (10.7 g, 30 mmol), and tetrakis(triphenylphosphine) palladium (Pd) (500 mg) in dry dioxane (100 mL) was heated under nitrogen at reflux (100–110° C.) for 24 hours (h). The solvent was evaporated under reduced pressure, the solid was dissolved in toluene, the solution was passed through celite to remove Pd. The solution was evaporated, and the solid was filtered to give 1 in 80.6% yield, mp 116.5–117° C. (hexanes/ether). $^1H$ nmr (DMSO-$d_6$); δ 6.71 (dd, J=3.6, 1.8 Hz, 1H), 7.32 (d, J=3.6 Hz, 1H), 7.85 (d, J=8.1 Hz, 1H), 7.94 (d, J=1.8 Hz, 1H), 8.29 (dd, J=8.1, 2.1 Hz, 1H), 8.96 (d, J=2.1 Hz, 1H). $^{13}C$ nmr; δ 152.7, 151.6, 150.8, 146.1, 140.8, 117.8, 117.2, 112.9, 112.5, 106.5. Calcd for $C_{10}H_6N_2O$: C, 70.58; H, 3.55. Found. C, 70.51; H, 3.49.

6-(5-Bromo-furan-2-yl)-nicotinonitrile (2). Continuing with Scheme 1, to a solution of 1 (5.1 g, 30 mmol) in DMF (20 mL) was added portionwise N-bromosuccinimide (5.87 g, 33 mmol) with stirring. The reaction mixture was stirred overnight, then poured onto cold-water. The precipitate that formed was collected, washed with water and dried to give the analytically pure product 2 in 90.4% yield, mp 196° C. $^1H$ nmr (DMSO-$d_6$); δ 6.86 (d, J=3.6 Hz, 1H), 7.38 (d, J=3.6 Hz, 1H), 7.86 (d, J=8.1 Hz, 1H), 8.33 (dd, J=8.1, 2.1 Hz, 1H). 8.98 (d, J=2.1 Hz, 1H). $^{13}C$ nmr; δ 153.4, 152.7, 149.6, 140.9, 125.4, 117.9, 117.0, 115.0, 114.9, 106.9. MS (m/z, rel.int.); 248 ($M^+$, 100), 220 (10), 169 (25), 141 (80), 114 (30). Calcd for $C_{10}H_5BrN_2O$: C, 48.22; H, 2.02; N, 11.25. Found. C, 48.47; H, 2.01; N, 11.34.

6-[5-(4-Cyano-phenyl)-furan-2-yl]-nicotinonitrile (3). Procedure: J. Org. Chem. 49(26), 5237 (1984). Continuing with Scheme 1, a stirred solution of 2 (1.245 g, 5 mmol), and tetrakis(triphenylphosphine) palladium (288 mg) in toluene (10 mL) under a nitrogen atmosphere was added 5 mL of a 2 M aqueous solution of $Na_2CO_3$ followed by 4-cyanophenyl boronic acid (821 mg, 4.6 mmol) in 5 mL of methanol. The vigorously stirred mixture was warmed to 80° C. for 24 h, and then cooled, and the precipitate was filtered. The precipitate was partitioned between methylene chloride (300 mL) and 2 M aqueous $Na_2CO_3$ (25 mL) containing 3 mL of concentrated ammonia. The organic layer was dried ($Na_2SO_4$), and then concentrated to dryness under reduced pressure to afford 3 in 76% yield; mp 301–302° C. (DMF). $^1H$ nmr (DMSO-$d_6$); δ 7.44 (d, J=3.6 Hz, 1H), 7.49 (d, J=3.6 Hz, 1H), 7.92 (d, J=8.4 Hz, 2H), 8.07 (d, J=8.4 Hz, 2H). 8.12 (d, J=8.4 Hz 1H), 8.36 (dd, J=8.4, 1.5 Hz, 1H), 9.0 (d, J=1.5 Hz, 1H). $^{13}C$ nmr; δ 153.4, 152.6, 152.3, 150.1, 140.7, 133.1, 132.7, 124.4, 118.3, 116.9, 114.6, 111.8, 110.2, 106.7. MS (m/z, rel.int.); 271 ($M^+$, 100), 243 (10), 140 (20), 103 (20). High resolution mass calcd. for $C_{17}H_9N_3O$: 271.07456. Observed 271.07392. Calcd. for $C_{17}H_9N_3O$: C, 75.26; H, 3.34; N. 15.49. Found. C, 74.95; H, 3.43; N, 15.23.

N-Hydroxy-6-{5-[4-(N-hydroxycarbamimidoyl)-phenyl]-furan-2-yl}-nicotinamidine (4). Continuing with Scheme 1, a mixture of hydroxylamine hydrochloride (10.4 g, 150 mmol, 10 eq.) in anhydrous DMSO (80 mL) was cooled to 5° C. under nitrogen and potassium t-butoxide (KO-t-Bu) (16.8 g, 150 mmol, 10 eq.) was added in portions. The mixture was stirred for 30 min. This mixture was added to the bis cyanoderivative 3 (15 mmol, 1 eq.). The reaction mixture was stirred overnight at room temperature. The reaction mixture was then poured slowly onto ice-water (200 mL water and 200 mL ice). The precipitate was filtered and washed with water and then ethanol to afford (4) (free base) in 91% yield; mp 252–253° C. $^1$H nmr (DMSO-$d_6$); δ 5.87 (s, 2H), 6.01 (s, 2H), 7.20 (d, J=3.6 Hz, 1H), 7.26 (d, J=3.6 Hz, 1H), 7.77 (d, J=8.1 Hz, 2H), 7.86 (d, J=8.1 Hz, 2H). 7.92 (d, J=8.1 Hz, 1H), 8.10 (dd, J=8.1, 2.1 Hz, 1H), 8.88 (d, J=2.1 Hz, 1H), 9.72 (s, 1H), 9.89 (s, 1H). $^{13}$C nmr; δ 153.7, 152.5, 150.3, 148.7, 148.1, 146.7, 133.6, 132.6, 130.0, 127.2, 125.8, 123.4, 117.8, 111.7, 109.0. MS (m/z, rel.int.); 337 (M$^+$, 100), 312 (10), 273 (5), 137 (20), 109 (30). High resolution mass calcd. for $C_{17}H_{15}N_5O_3$: 337.11749. Observed 337.11560.

Salt of (4). Mp 281–282° C.$^{dec}$. Calcd for $C_{17}H_{15}N_5O_3$-3HCl-0.8H$_2$O: C, 44.27; H, 4.28; N, 15.18; Cl, 23.06. Found C, 44.28; H, 4.26; N, 15.14; Cl, 22.87. $^{13}$C nmr; δ 158.7, 156.8, 153.6, 152.4, 151.0, 148.8, 137.2, 133.6, 128.8, 124.4, 124.2, 120.1, 118.2, 114.2, 111.6.

N-Methoxy-6-{5-[4-(N-methoxy-carbamimidoyl)-phenyl]-furan-2-yl}-nicotinamidine (5). Continuing with Scheme 1, to a solution of 4 (10 mmol) in dioxane (15 mL) and 2 N NaOH (80 mL) at 0–5° C., was slowly added dimethylsulfate (30 mmol) in dioxane (5 mL). The reaction mixture was further stirred for 2 h and then extracted with ethylacetate (500 mL, 3 times). The solvent was evaporated and the residue was purified (SiO$_2$, hexanes/EtOAc, 40:60) to give 5 (free base) in 50% yield; mp 166–167 ° C. $^1$H nmr (DMSO-$d_6$); δ 3.77 (s, 3H), 3.80 (s, 3H), 6.12 (s, 2H), 6.28 (s, 2H), 7.23 (d, J=3.6 Hz, 1H), 7.29 (d, J=3.6 Hz, 1H), 7.75 (d, J=8.4 Hz, 2H), 7.87 (d, J=8.4 Hz, 2H). 7.92 (d, J=8.1 Hz, 1H), 8.10 (d, J=8.1 Hz, 1H), 8.84 (s, 1H). $^{13}$C nmr; δ 153.6, 152.5, 150.5, 149.0, 148.5, 146.9, 134.1, 131.8, 130.3, 126.5, 126.2, 123.5, 117.8, 112.0, 109.3, 60.7, 60.6. MS (m/z, rel.int.); 365 (M$^+$, 100), 334 (20), 318 (20), 287 (35). High resolution mass Calcd. for $C_{19}H_{19}N_5O_3$: 365.14879. Observed: 365.14927.

Salt of (5). Mp 196–198° C.$^{dec}$. Calcd. for $C_{19}H_{19}N_5O_3$-3HCl-1H$_2$O: C, 46.30; H, 4.90; N, 14.21; Cl, 21.58. Found C, 45.95; H, 4.83; N, 14.00; Cl, 21.53.

N-Acetoxy-6-{5-[4-(N-Acetoxycarbamimid yl)-phenyl]-furan-2-yl}-nicotinamidine (6). Procedure: *Synthetic Communications* 26(23), 4351–4367 (1996). Continuing with Scheme 1, to a solution of 4 (337 mg, 1 mmol) in glacial acetic acid (10 mL) was slowly added acetic anhydride (0.35 mL). After stirring for overnight TLC indicated complete acylation of the starting material. The reaction mixture was poured onto ice water, and the precipitate was filtered, washed with water and dried to give 6 in 98% yield, mp 283° C. $^1$H nmr (DMSO-$d_6$); δ 2.18 (s, 6H), 6.85 (s, 2H), 7.05 (s, 2H), 7.25 (d, J=3.6 Hz, 1H), 7.29 (d, J=3.6 Hz, 1H), 7.82 (d, J=8.1 Hz, 2H), 7.95 (d, J=8.1 Hz, 2H). 8.00 (d, J=8.1 Hz, 1H), 8.20 (dd, J=8.1, 1.8 Hz, 1H), 8.90 (d, J=1.8 Hz, 1H). $^{13}$C nmr; δ 168.49, 168.45, 155.9, 154.4, 153.7, 152.5, 149.4, 147.8, 135.4, 131.3, 130.9, 127.3, 125.7, 123.7, 117.9, 112.6, 109.98, 19.88, 19.84. Calcd. for $C_{21}H_{19}N_5O_5$-0.25CH$_3$CO$_2$H: C, 59.17; H, 4.61; N, 16.04. Found C, 58.89; H, 4.53; N, 16.09.

6-[5-(4-Carbamimidoyl-phenyl)-furan-2-yl]-nicotinamidine acetate salt (7). Procedure: *Synthetic communications* 26(23):4351–4367 (1996). Continuing with Scheme 1, to a solution of 6 (330 mg, 0.784 mmol) in glacial acetic acid (13 mL), and ethanol (20 mL) was added 10% palladium on carbon (Pd/C) (80 mg). The mixture was placed on Parr hydrogenation apparatus at 50 psi for 4 h at room temperature. The mixture was filtered through HYFLO® matrix and the filter pad washed with water. The filtrate was evaporated under reduced pressure and the precipitate was collected and washed with ether to give 7 in 84% yield, mp 264–266° C.$^{dec}$. $^1$H nmr (DMSO-$d_6$); δ 1.80 (s, 6H), 7.43 (s, 2H), 7.89 (d, J=8.1 Hz, 2H), 8.08 (d, J=8.1 Hz, 2H), 8.11 (d, J=7.8 Hz, 1H), 8.26 (d, J=7.8 Hz, 1H), 8.98 (s, 1H). $^{13}$C nmr (D$_2$O/DMSO-$d_6$); δ 166.7, 165.1, 155.4, 153.0, 152.7, 149.7, 138.9, 135.5, 130.0, 128.1, 125.9, 123.9, 120.5, 116.5, 113.0, 25.0, 20.4. Calcd. for $C_{17}H_{15}N_5O$-2.0CH$_3$CO$_2$H-1.7H$_2$O: C, 55.30; H, 5.83; N, 15.35. Found. C, 55.30; H, 5.78; N, 15.15.

6-[5-(4-Carbamimidoyl-phenyl)-furan-2-yl]-nicotinamidine (7). Continuing with Scheme 1, base 7 was prepared by dissolving 7 (50 mg) in water (5 mL) and by neutralization with 1 N NaOH. The precipitate was filtered, dried to afford free amidine of 7, mp 232° C. $^1$H nmr (DMSO-$d_6$); δ 7.39 (s, 2H), 7.89 (d, J=8.1 Hz, 2H), 8.05 (d, J=8.1 Hz, 3H), 8.25 (d, J=8.1 Hz, 1H), 8.99 (s, 1H). MS (m/z, rel.int.); 306 (M$^+$+1, 100), 289 (10), 236 (10). High resolution mass calcd. for $C_{17}H_{16}N_5O$: 306.13549. Observed: 306.13583.

6-(Thiophen-2-yl)nicotinonitrile (8). Referring now to Scheme 2, the same procedure described for 1 was used employing 2-tributyltin thiophene instead of 2-tributyltin furan. Yield 82%, mp 110–111° C. (hexanes/ether). $^1$H nmr (DMSO-$d_6$); δ 7.24 (dd, J=3.9, 2.1 Hz, 1H), 7.83 (d, J=3.9 Hz, 1H), 8.02 (d, J=2.1 Hz, 1H), 8.13 (d, J=8.4 Hz, 1H), 8.32 (dd, J=8.4, 2.1 Hz, 1H), 8.95 (d, J=2.1 Hz, 1H). $^{13}$C nmr; δ 154.7, 152.5, 142.7, 140.5, 131.2, 128.9, 128.2, 118.4, 117.2, 106.4. Calcd. for $C_{10}H_6N_2S$: C, 64.49; H, 3.24. Found. C, 64.54; H, 3.20.

6-(5-Bromo-thiophen-2-yl)nicotinonitrile (9). Continuing with Scheme 2, the same procedure described for 2 was used starting with 8. Yield 95%, mp 172–173° C. $^1$H nmr (DMSO-$d_6$); δ 7.38 (d, J=3.9 Hz, 1H), 7.88 (d, J=3.9 Hz, 1H), 8.14 (d, J=8.4 Hz, 1H), 8.35 (dd, J=8.4, 2.1 Hz, 1H), 8.94 (d, J=2.1 Hz, 1H). $^{13}$C nmr; δ 153.7, 152.6, 144.3, 140.9, 132.4, 128.9, 118.1, 117.3, 117.1, 106.9. Calcd. For $C_{10}H_5BrN_2S$: C, 45.30; H, 1.90. Found. C, 45.30; H, 1.86.

6-[5-(4-Cyano-phenyl)-thiophen-2-yl]nicotinonitrile (10). Continuing with Scheme 2, the same procedure described for 3 was used starting with 9. Yield 77.7%; mp 316–318° C. (DMF). $^1$H nmr (DMSO-$d_6$); δ 7.84 (d, J=3.9 Hz, 1H), 7.90 (d, J=8.7 Hz, 2H), 7.96 (d, J=8.7 Hz, 2H), 8.07 (d, J=3.9 Hz, 1H). 8.18 (d, J=8.4 Hz, 1H), 8.34 (dd, J=8.4 Hz, J=2.1 Hz, 1H), 8.97 (d, J=2.1 Hz, 1H). Calcd. for $C_{17}H_9N_3S$: C, 71.05; H, 3.15. Found. C, 70.73; H, 3.21.

N-Hydroxy-6-{5-[4-(N-hydroxycarbamimidoyl)-phenyl]-thiophen-2-yl}-nicotinamidine (11). Continuing with Scheme 2, the same procedure described for 4 was used starting with 10. Yield 97%; mp 293–295° C.$^{dec}$. $^1$H nmr (DMSO-$d_6$); δ 5.86 (s, 2H), 6.01 (s, 2H), 7.64 (d, J=3.9 Hz, 1H), 7.74 (m, 4H), 7.86 (d, J=3.9 Hz, 1H), 7.98 (d, J=8.7 Hz, 1H). 8.06 (dd, J=8.7, 1.8 Hz, 1H), 8.82 (d, J=1.8 Hz, 1H), 9.73 (s, 1H), 9.89 (s, 1H). $^{13}$C nmr; δ 151.5, 150.2, 148.7, 146.3, 144.8, 143.4, 133.8, 133.5, 132.7, 127.3, 126.8, 126.0, 125.2, 124.9, 117.8.

Salt f (11). mp 301–303° C.$^{dec}$. Calcd for $C_{17}H_{15}N_5O_2S$-3HCl-1H$_2$O: C, 42.46; H, 4.19; N, 14.56. Found. C, 42.37; H, 4.32; N, 14.22.

N-Methoxy-6-{5-[4-(N-methoxy-carbamimidoyl)-phenyl]-thioph n-2-yl}-nicotinamidine (12). Continuing with Scheme 2, the same procedure described for 5 was used starting with 11. Yield 52%; mp 188–189° C. $^1$H nmr (DMSO-$d_6$); δ 3.76 (s, 3H), 3.79 (s, 3H), 6.16 (s, 2H), 6.28 (s, 2H), 7.65 (d, J=3.9 Hz, 1H), 7.71–7.78 (m, 4H), 7.88 (d, J=3.9 Hz, 1H), 7.98 (d, J=8.4 Hz, 1H). 8.05 (dd, J=8.4, 2.1 Hz, 1H), 8.78 (d, J=2.1 Hz, 1H). $^{13}$C nmr; δ 151.9, 150.4, 148.9, 146.5, 144.8, 143.4, 134.2, 134.0, 131.8, 127.0, 126.5, 126.3, 125.4, 124.9, 117.8, 60.7, 60.6.

Salt of (12). Mp 230–231° C.$^{dec}$. Calcd. for $C_{19}H_{19}N_5O_2S$-3HCl-0.3EtOH: C, 46.65; H, 4.75; N, 13.87. Found. C, 47.05; H, 4.92; N, 13.87.

5-Bromo-pyridine-2-carbonitrile: Referring now to Scheme 3, a mixture of 2,5-dibromopyridine (20 mmol) and Cu(1)CN (20 mmol) in DMF (120 mL) was refluxed for 12 hr at 120° C. The reaction mixture was poured onto water and the solid which formed was extracted by using ethylacetate (250 mL, 3 times). The solvent was evaporated and the precipitate purified ($SiO_2$, hexanes/EtOAc 90:10). Yield 74%, mp 125–126° C. $^1$H nmr (DMSO-$d_6$); δ 8.03 (d, J=8.1 Hz, 1H), 8.37 (dd, J=8.1, 2.1 Hz, 1H). 8.92 (d, J=2.1 Hz, 1H). $^{13}$C nmr; δ 152.2, 140.6, 131.1, 130.3, 125.1, 117.0.

5-(Furan-2-yl)pyridine-2-carbonitrile (14). Continuing with Scheme 3, the same procedure described for 1 was used starting with 5-Bromo-pyridine-2-carbonitrile. Yield 83%, mp 115–116° C. $^1$H nmr (DMSO-$d_6$); δ 6.74 (dd, J=3.6, 1.8 Hz, 1H), 7.40 (d, J=3.6 Hz, 1H), 7.96 (d, J=1.8 Hz, 1H), 8.08 (d, J=8.1 Hz, 1H), 8.27 (dd, J=8.1, 2.1 Hz, 1H). 9.11 (d, J=2.1 Hz, 1H). $^{13}$Cnmr; δ 148.8, 146.0, 145.6, 131.1, 130.1, 129.2, 129.1, 117.6, 112.8, 110.9. Calcd for $C_{10}H_6N_2O$: C, 70.58; H, 3.55; N, 16.46. Found. C, 70.40; H, 3.60; N, 16.35.

5-(5-Bromo-furan-2-yl)pyridine-2-carbonitrile (15). Continuing with Scheme 3, the same procedure described for 2 was used starting with 14. Yield 93%, mp 173° C. $^1$H nmr (DMSO-$d_6$); δ 6.85 (d, J=3.6 Hz, 1H), 7.43 (d, J=3.6 Hz, 1H), 8.06 (d, J=8.4 Hz, 1H), 8.23 (dd, J=8.4, 2.1 Hz, 1H). 9.06 (d, J=2.1 Hz, 1H). $^{13}$C nmr; δ 150.9, 145.8, 131.0, 130.4, 129.2, 128.1, 124.8, 117.5, 114.9, 113.4. Calcd for $C_{10}H_5BrN_2O$: C, 48.22; H, 2.02; N, 11.25. Found. C, 48.34; H, 2.10; N, 11.13.

5-[5-(4-Cyano-phenyl)-furan-2-yl]-pyridine-2-carbonitrile (16). Continuing with Scheme 3, to a stirred solution of 15 (1.245 g, 5 mmol), and tetrakis(triphenylphosphine) palladium (288 mg) in toluene (15 mL) under a nitrogen atmosphere was added 10 mL of a 1 M aqueous solution of $NaHCO_3$ followed by 4-cyanophenyl boronic acid (821 mg, 4.6 mmol) in 5 mL of methanol. The vigorously stirred mixture was warmed to 80° C. for 24 h, then cooled, and the precipitate was filtered. The precipitate was partitioned between methylene chloride (300 mL) and 1 M aqueous $NaHCO_3$ (50 mL). The organic layer was dried ($Na_2SO_4$), and then concentrated to dryness under reduced pressure to afford 16 in 64% yield; mp 276–277° C. (DMF). $^1$H nmr (DMSO-$d_6$); δ 7.49 (d, J=3.6 Hz, 1H), 7.59 (d, J=3.6 Hz, 1H), 7.95 (d, J=8.7 Hz, 2H), 8.10 (d, J=8.7 Hz, 2H). 8.14 (d, J=8.1 Hz 1H), 8.49 (dd, J=8.1, 1.5 Hz, 1H), 9.29 (d, J=1.5 Hz, 1H). $^{13}$C nmr; δ 153.0, 149.7, 146.3, 133.1, 132.8, 131.4, 130.4, 129.0, 128.5, 124.4, 118.6, 117.4, 113.2, 111.8, 110.0. Calcd. for $C_{17}H_9N_3O$: C, 75.26; H, 3.34; N, 15.49. Found. C, 75.02; H, 3.35; N, 15.39.

N-Hydroxy-5-{5-[4-(N-hydroxycarbamimidoyl)-phenyl]-furan-2-yl}-pyridine-2-carboxamidine (17). Continuing with Scheme 3, the same procedure described for 4 was used starting with 16. Yield 93%; mp 276–279° C.

$^1$H nmr (DMSO-$d_6$); δ 5.85 (s, 4H), 7.20 (d, J=3.3 Hz, 1H), 7.31 (d, J=3.3 Hz, 1H), 7.77 (d, J=8.4 Hz, 2H), 7.88 (d, J=8.4 Hz, 2H). 7.92 (d, J=8.4 Hz, 1H), 8.21 (dd, J=8.4, 1.8 Hz, 1H), 9.04 (d, J=1.8 Hz, 1H), 9.72 (s, 1H), 10.0 (s, 1H). $^{13}$C nmr; δ 153.3, 150.3, 149.9, 149.2, 148.4, 143.4, 132.5, 130.9, 130.0, 126.0, 125.8, 123.3, 119.4, 110.3, 108.9. MS (m/z, rel.int.); 337 (M$^+$, 40), 322 (25), 288 (100), 272 (95), 246 (25). High resolution mass calcd. for $C_{17}H_{15}N_5O_3$: 337.11749. Observed 337.11544.

Salt of (17). Mp 257–260° C. Calcd. for $C_{17}H_{15}N_5O_3$-2HCl-0.9$H_2O$: C, 47.87; H, 4.44; N, 16.42. Found C, 47.99; H, 4.27; N, 16.10.

N-Methoxy-5-{5-[4-(N-methoxycarbamimidoyl)-phenyl]-furan-2-yl}-pyridin-2-carboxamidine (18). Continuing with Scheme 3, the same procedure described for 5 was used starting with 17. Yield 50%; mp 142–143° C.

$^1$H nmr (DMSO-$d_6$); δ 3.78 (s, 3H), 3.82 (s, 3H), 6.11 (s, 4H), 7.20 (s, 1H), 7.33 (s, 1H), 7.77 (d, J=8.4 Hz, 2H), 7.87 (d, J=8.4 Hz, 2H). 7.92 (d, J=8.1 Hz, 1H), 8.22 (dd, J=8.1, 2.1 Hz, 1H), 9.03 (d, J=2.1 Hz, 1H). $^{13}$C nmr; δ 153.3, 150.5, 149.9, 149.0, 147.4, 143.5, 131.6, 131.0, 130.3, 126.3, 126.2, 123.3, 119.8, 110.6, 109.1, 61.1, 60.6.

Salt of (18). Mp 235–237° C. Calcd. for $C_{19}H_{19}N_5O_3$-2HCl: C, 52.06; H, 4.82; N, 15.97, Cl, 16.17. Found C, 51.91; H, 4.82; N, 16.08; Cl, 15.91.

N -Acetoxy-5-{5-[4-(N-Acetoxycarbamimidoyl)-phenyl]-furan-2-yl}-pyridine-2-carboxamidine (19). Continuing with Scheme 3, the same procedure described for 6 was used starting with 17. Yield 89%, mp 267–270° C.

$^1$H nmr (DMSO-$d_6$); δ 2.17 (s, 3H), 2.19 (s, 3H), 6.88 (s, 2H), 6.95 (s, 2H), 7.31 (d, J=3.3 Hz, 1H), 7.43 (d, J=3.3 Hz, 1H), 7.82 (d, J=8.4 Hz, 2H), 7.95 (d, J=8.4 Hz, 2H). 8.01 (d, J=8.7 Hz, 1H), 8.33 (dd, J=8.7, 2.1 Hz, 1H), 9.13 (d, J=2.1 Hz, 1H). $^{13}$C nmr; δ 168.4, 168.2, 155.9, 153.8, 153.3, 149.9, 146.6, 143.9, 131.3, 130.7, 128.2, 127.3, 123.5, 121.0, 111.2, 109.7, 19.9, 19.8. Calcd for $C_{21}H_{19}N_5O_5$: C, 59.85; H, 4.54. Found. C, 59.62; H, 4.47.

5-[5-(4-Carbamimidoyl-phenyl)-furan-2-yl]-pyridine-2-carboxamidine actate salt (20): Continuing with Scheme 3, to a solution of 19 (380 mg, 0.90 mmol) in glacial acetic acid (13 mL), and ethanol (25 mL) was added 10% palladium on carbon (120 mg). The mixture was placed on Parr hydrogenation apparatus at 50 psi for 4 h at room temperature. The mixture was filtered through HYFLO® matrix (available from Word Minerals Corporation of Santa Barbara, Calif., United States of America) and the filter pad washed with water. The filtrate was evaporated under reduced pressure and the precipitate was collected and washed with ether to give 20, in 68% yield, mp 266–268° C.$^{dec}$.

$^1$H nmr (DMSO-$d_6$); δ 1.80 (s, 9H), 7.41 (d, J=3.6 Hz, 1H), 7.51 (d, J=3.6 Hz, 1H), 7.94 (d, J=8.7 Hz, 2H), 8.12 (d, J=8.7 Hz, 2H), 8.28 (d, J=8.4 Hz, 1H), 8.51 (d, J=8.4 Hz, 1H), 9.28 (s, 1H). Calcd. for $C_{17}H_{15}N_5O$-3$CH_3CO_2H$-2.1$H_2O$: C, 52.78; H, 6.00; N, 13.38. Found C, 52.43; H, 5.62; N, 13.75.

2,5-Bis(5-cyano-2-pyridyl)furan (21). Referring now to Scheme 4, a mixture of 6-chloronicotinonitrile (1.38 g, 10 mmol), 2,5-bis(tri-n-butylstannyl)furan (3.2 g, 5 mmol) and tetrakis(triphenyl-phosphine)palladium(0) (125 mg) in dry 1,4-dioxane (40 mL) was heated under nitrogen at reflux (100–110° C.) for 24 h. The solvent was evaporated under reduced pressure and the residue was dissolved in methylene chloride and the solution was passed through CELITE® matrix (available from Word Minerals Corporation of Santa Barbara, Calif., United States of America) to remove Pd. The solution was evaporated, filtered and the precipitate was washed with hexanes to afford 21 in 85% yield, mp 311–312° C. (DMF). $^1$H nmr (DMSO-$d_6$); δ 7.55 (s, 2H), 8.20 (d, J=8.4 Hz, 2H), 8.44 (dd, J=8.4, 2.1 Hz, 2H). 9.06 (d, J=2.1 Hz, 2H). $^{13}$C nmr; δ 153.5, 152.8, 150.0, 141.0, 118.8, 117.1, 114.8, 107.3. Calcd. for $C_{16}H_8N_4O$: C, 70.58; H, 2.96; N, 20.57. Found. C, 70.35; H, 3.04; N, 20.35.

2,5-Bis[5-(N-hydroxycarbamimidoyl)-2-pyridyl]furan (22). Continuing with Scheme 4, the same procedure described for 4 was used starting with 21. Yield 96%, mp 272–274° C.$^{dec}$. $^1$H nmr (DMSO-d$_6$); δ 6.00 (s, 4H), 7.31 (s, 2H), 7.96 (d, J=8.4 Hz, 2H), 8.13 (dd, J=8.4, 2.1 Hz, 2H). 8.91 (d, J=2.1 Hz, 2H), 9.88 (s, 2H). $^{13}$C nmr; δ 153.5, 148.7, 147.9, 146.7, 133.6, 127.6, 118.0, 111.7. MS (m/z, rel.int.); 338 (M$^+$, 40), 306 (45), 289 (100), 246 (10), 219 (15), 141 (45), 103 (88). High resolution mass calcd. for $C_{16}H_{14}N_6O_3$: 338.11274. Observed 338.11255. MA-199 salt (22, DB 840). Mp 283–285° C.$^{dec}$. Calcd. for $C_{16}H_{14}N_6O_3$-3.65HCl-1H$_2$O: C, 39.27; H, 4.04; N, 17.17; Cl, 26.44. Found C, 39.67; H, 4.04; N, 16.89; Cl, 26.46.

2,5-Bis[5-(N-acetoxycarbamimidoyl)-2-pyridyl]furan (23). Continuing with Scheme 4, the same procedure described for 6 was used starting with 22. Yield 94%, mp 299–300° C. $^1$H nmr (DMSO-d$_6$); δ 2.18 (s, 6H), 6.95 (s, 4H), 7.38 (s, 2H), 8.03 (d, J=8.4 Hz, 2H), 8.19 (dd, J=8.4, 2.1 Hz, 2H), 8.92 (d, J=2.1 Hz, 2H). $^{13}$C nmr; δ 168.2, 154.2, 153.5, 149.1, 147.7, 135.2, 126.0, 118.1, 112.4, 19.6. Calcd for $C_{20}H_{18}N_6O_5$: C, 56.86; H, 4.29. Found. C, 56.45; H, 4.25.

2,5-Bis[5-amidine-2-pyridyl]furan (24). Continuing with Scheme 4, the free amidine 24 prepared by dissolving 24.AcOH salt prepared via the same procedure described for 7 starting with 23, (230 mg) in water (10 mL) and neutralization with 1N NaOH. The precipitate was filtered and dried to give free amidine of 24 (108 mg), mp 239–241° C. MS (m/z, rel.int.); 307 (M$^+$+1, 90), 247 (25), 237 (100).

HCl salt (24): mp 316–317° C. $^1$H nmr (DMSO-d$_6$); δ 7.56 (s, 2H), 8.22 (d, J=8.7 Hz, 2H), 8.33 (dd, J=8.7 Hz, J=2.1 Hz, 2H). 8.96 (d, J=2.1 Hz, 2H). $^{13}$C nmr; δ 165.3, 154.4, 152.7, 149.8, 139.1, 124.6, 121.1, 116.3. Calcd. for $C_{16}H_{14}N_6O$-3.3HCl-2.2H$_2$O: C, 41.23; H, 4.69; N, 18.00; Cl, 25.02. Found C, 41.61; H, 4.64; N, 17.62; Cl, 24.89.

6-Chloro-N-hydroxy-nicotinamidine (25). Referring now to Scheme 5, the same procedure described for 4 was used starting with 6-chloronicotinonitrile. Yield 93%, mp 185–186° C. (EtOAc). $^1$H nmr (DMSO-d$_6$); δ 6.05 (s, 2H), 7.54 (d, J=8.4 Hz, 1H), 8.07 (dd, J=8.4, 2.4 Hz, 1H). 8.67 (d, J=2.4 Hz, 1H), 9.95 (s, 1H). $^{13}$C nmr; δ 150.2, 147.9, 146.6, 136.3, 128.5, 123.7.

6-Chloro-N-methoxy-nicotinamidine (26). Continuing with Scheme 5, the same procedure described for 5 was used starting with 25. Yield 70%, mp 105–105.5° C. (hexanes). $^1$H nmr (DMSO-d$_6$); δ 3.79 (s, 3H), 6.32 (s, 2H), 7.55 (d, J=8.4 Hz, 1H), 8.06 (dd, J=8.4 Hz, J=2.4 Hz, 1H). 8.65 (d, J=2.4 Hz, 1H). $^{13}$C nmr; δ 150.6, 148.1, 146.9, 136.7, 127.7, 123.8, 60.7. Calcd for $C_7H_8ClN_3O$: C, 45.29; H, 4.34; N, 22.63. Found. C, 45.56; H, 4.32; N, 22.47.

2,5-Bis[5-(N-methoxycarbamimidoyl)-2-pyridyl]furan (27). Continuing with Scheme 5, a mixture of 26 (6, mmol), 2,5-bis(tri-n-butylstannyl)furan (3 mmol) and tetrakis(triphenylphosphine)-palladium(0) (150 mg) in dry 1,4-dioxane (20 mL) was heated under nitrogen at reflux (100–110° C.) for 24 h. The solvent was evaporated under reduced pressure, dissolved in methylene chloride, and the solution was passed through celite to remove Pd. The solution was evaporated, the solid was filtered and washed with hexanes to afford 27 (SiO$_2$, hexanes/EtOAc, 1:1), yield 35%, mp 228–230° C. $^1$H nmr (DMSO-d$_6$); δ 3.80 (s, 6H), 6.31 (s, 4H), 7.34 (s, 2H), 7.98 (d, J=8.4 Hz, 2H), 8.13 (dd, J=8.4, 2.4 Hz, 2H). 8.88 (d, J=2.4 Hz, 2H). $^{13}$C nmr; δ 153.5, 148.9, 148.3, 147.0, 134.1, 126.8, 118.1, 112.0, 60.7. MS (m/z, rel.int.); 366 (M$^+$, 100), 335 (25), 319 (30), 288 (40). High resolution mass calcd. for $C_{18}H_{18}N_6O_3$: 366.14404. Observed: 366.14012.

Salt (27). Mp 201–202° C.$^{dec}$. Calcd. for $C_{18}H_{18}N_6O_3$-3.25HCl-3H$_2$O-0.1C$_2$H$_5$OH: C, 40.21; H, 5.16; N, 15.46; Cl, 21.19. Found C, 40.18; H, 5.01; N, 15.08; Cl, 20.99.

6-[5-(4-Cyano-2-methyl-phenyl)-furan-2-yl]-nicotinonitrile (28). Referring now to Scheme 6, a mixture of 1 (680 mg, 4 mmol), 4-bromo-3-methylbenzonitrile (784 mg, 4 mmol), tetrakis(triphenylphosphine)-palladium(0) (228 mg) and potassium acetate (981.5 mg, 10 mmol) in dry DMF (15 mL) was heated under nitrogen at 120° C. for 16 h. The reaction mixture then poured onto cold-water. The precipitate that formed was collected, dissolved in methylene chloride, and the solution was passed through celite to remove Pd. The solution was evaporated, the solid was filtered and purified to afford 28 (SiO$_2$, hexanes/EtOAc, 1:1), yield 40%, mp 233–234° C. $^1$H nmr (DMSO-d$_6$); δ 2.61 (s, 3H), 7.25 (d, J=3.6 Hz, 1H), 7.51 (d, J=3.6 Hz, 1H), 7.77 (d, J=8.1 Hz, 1H), 7.82 (s, 1H). 8.03–8.07 (m, 2H), 8.36 (dd, J=8.1, 2.1 Hz, 1H), 9.02 (d, J=2.1 Hz, 1H). $^{13}$C nmr; δ 153.2, 152.7, 151.9, 150.2, 140.8, 135.6, 134.8, 132.5, 129.8, 127.3, 118.3, 117.0, 114.4, 110.2, 106.8, 21.2.

N-Hydroxy-6-{5-[4-(N-hydroxycarbamimidoyl)-2-methyl-phenyl]-furan-2-yl}-nicotinamidine (29). Continuing with Scheme 6, the same procedure described for 4 was used starting with 28. Yield 98%; mp 196–198° C. $^1$H nmr (DMSO-d$_6$); δ 2.60 (s, 3H), 5.84 (s, 2H), 6.04 (s, 2H), 7.01 (d, J=3.6 Hz, 1H), 7.30 (d, J=3.6 Hz, 1H), 7.63 (d, J=8.4 Hz, 1H), 7.66 (s, 1H). 7.85–7.89 (m, 2H), 8.11 (dd, J=8.4, 2.1 Hz, 1H), 8.88 (d, J=2.1 Hz, 1H), 9.70 (s, 1H), 9.92 (s, 1H).

N-Acetoxy-6-{5-[4-(N-acetoxycarbamimidoyl)-2-methyl-phenyl]-furan-2-yl}-nicotinamidine (30). Continuing with Scheme 6, the same procedure described for 6 was used starting with 29. Yield 95%, mp 203–205° C. $^1$H nmr (DMSO-d$_6$); δ 2.15 (s, 3H), 2.16 (s, 3H), 2.61 (s, 3H), 6.86 (s, 2H), 7.04 (s, 2H), 7.10 (d, J=3.6 Hz, 1H), 7.39 (d, J=3.6 Hz, 1H), 7.67 (d, J=8.4 Hz, 1H), 7.71 (s, 1H). 7.94–7.98 (m, 2H), 8.17 (dd, J=8.4, 2.1 Hz, 1H), 8.91 (d, J=2.1 Hz, 1H).

6-[5-(4-Carbamimidoyl-2-methyl-phenyl)-furan-2-yl]-nicotinamidin ac tate salt (31). Continuing with Scheme 6, the same procedure described for 7 was used starting with 30. Yield 66%, mp 226–229° C.$^{dec}$. $^1$H NMR (DMSO-d$_6$); δ 1.80 (s, 6H), 2.63 (s, 3H), 7.20 (d, J=3.6 Hz, 1H), 7.43 (d, J=3.6 Hz, 1H), 7.69 (d, 8.1 Hz, 1H), 7.79 (s, 1H), 8.04 (m, 2H), 8.27 (d, J=8.1 Hz, 1H), 8.98 (s, 1H). Calcd. for $C_{18}H_{17}N_5O$-2.0CH$_3$CO$_2$H-2.6H$_2$O-0.25EtOH: C, 54.28; H, 6.41; N, 14.06. Found C, 54.33; H, 6.33; N, 13.77.

6-(5-Styryl-furan-2-yl)-nicotinonitrile (32). Referring now to Scheme 7, the same procedure described for 3 was used employing trans-2-phenylvinyl boronic acid instead of p-cyanophenyl boronic acid. Yield 69%, mp 154–155° C. $^1$H nmr (DMSO-d$_6$); δ 6.79 (d, J=3.6 Hz, 1H), 7.18–7.62 (m, 8H), 8.01 (d, J=8.4 Hz, 1H), 8.34 (dd, J=8.4 Hz, 2.1 Hz, 1H), 8.98 (d, J=2.1 Hz, 1H). $^{13}$C nmr; δ 155.4, 152.8, 151.0, 150.4, 140.7, 136.2, 129.3, 128.8, 128.2, 126.6, 118.0, 117.3, 115.9, 114.9, 112.3, 106.2. Calcd. for $C_{18}H_{12}N_2O$: C, 79.39; H, 4.44; N, 10.28. Found C, 79.12; H, 4.58; N, 10.42.

N-Hydroxy-6-(5-styryl-furan-2-yl)-nicotinamidine (33). Continuing with Scheme 7, the same procedure described for 4 was used starting with 32. Yield 94%, mp 230–231° C. $^1$H nmr (DMSO-d$_6$); δ 6.02 (s, 2H), 6.73 (d, J=3.6 Hz, 1H), 7.20–7.61 (m, 8H), 7.86 (d, J=8.4 Hz, 1H), 8.09 (dd, J=8.4 Hz, 2.1 Hz, 1H), 8.87 (d, J=2.1 Hz, 1H), 9.90 (s, 1H). $^{13}$C nmr; δ 153.8, 152.3, 148.7, 148.1, 146.7, 136.4, 133.5, 128.8, 127.9, 127.8, 127.2, 126.5, 117.7, 116.2, 112.0, 111.6.

HCl salt (33). mp 224–226° C.$^{dec}$. Calcd. for C$_{18}$H$_{15}$N$_3$O$_2$·2HCl·0.5H$_2$O: C, 55.82; H, 4.68; N, 10.85. Found C, 55.88; H, 4.70; N, 10.72.

6-[5-(4-Cyanobenzyl)furan-2-yl]nicotinonitrile (35). Continuing with Scheme 7, a solution of 2 (996 mg, 4 mmol) in tetrahydrofuran (25 mL) was added palladium tetrakis(triphenyl-phosphine) (228 mg) and p-cyanobenzyl zinc bromide (12 mL, 0.5 M in THF, 6 mmol). The reaction mixture was stirred 24 h at room temperature. The mixture was diluted with dichloromethane, washed with saturated NH$_4$Cl and the organic layer was dried over anhydrous Na$_2$SO$_4$. After filtration and on concentration the residue was purified by chromatography (SiO$_2$), hexanes (100–40%)/EtOAc (0–60%), to afford 35 in 48% yield, mp 204–206° C. $^1$H nmr (DMSO-d$_6$); δ 4.23 (s, 2H), 6.46 (d, J=3.3 Hz, 1H), 7.27 (d, J=3.3 Hz, 1H), 7.51 (d, J=8.1 Hz, 2H), 7.77 (d, J=8.1 Hz, 2H), 7.79 (d, J=8.4 Hz, 1H), 8.25 (dd, J=8.4 Hz, 1.8 Hz, 1H), 8.92 (d, J=1.8 Hz, 1H). $^{13}$C nmr; δ 156.3, 152.6, 150.9, 150.6, 143.2, 140.5, 132.4, 129.6, 118.6, 117.5, 117.1, 113.5, 110.3, 109.5, 106.0, 33.5.

N-Hydroxy-6-{5-[4-(N-hydroxycarbamimidoyl)benzyl]-furan-2-yl}-nicotinamidine (36). Continuing with Scheme 7, the same procedure described for 4 was used starting with 35. Yield 85%, mp 214–216° C. $^1$H nmr (DMSO-d$_6$); δ 4.08 (s, 2H), 5.76 (s, 2H), 5.96 (s, 2H), 6.33 (d, J=3.3 Hz, 1H), 7.05 (d, J=3.3 Hz, 1H), 7.29 (d, J=8.4 Hz, 2H), 7.62 (d, J=8.4 Hz, 3H), 8.02 (dd, J=8.4 Hz, 2.1 Hz, 1H), 8.79 (d, J=2.1 Hz, 1H), 9.57 (s, 1H), 9.84 (s, 1H). $^{13}$C nmr; δ 155.7, 151.8, 150.6, 148.7, 148.4, 146.5, 138.5, 133.6, 131.7, 128.3, 126.9, 125.6, 117.1, 110.3, 109.3, 33.5.

N-Acetoxy-6-{5-[4-(N-acetoxycarbamimidoyl)benzyl]-furan-2-yl}-nicotinamidine (37). The same procedure described for 6 was used starting with 36. Yield 98%, mp 194–196° C. $^1$H nmr (DMSO-d$_6$); δ 2.15 (s, 3H), 2.17 (s, 3H), 4.17 (s, 2H), 6.37 (d, J=3.3 Hz, 1H), 6.71 (s, 2H), 6.92 (s, 2H), 7.13 (d, J=3.3 Hz, 1H), 7.39 (d, J=8.1 Hz, 2H), 7.66–7.70 (m, 3H), 8.09 (dd, J=8.4, 2.1 Hz, 1H), 8.83 (d, J=2.1 Hz, 1H). $^{13}$C nmr; 6168.3, 156.2, 156.0, 154.3, 151.6, 149.7, 147.6, 140.1, 135.2, 129.9, 128.5, 126.9, 125.2, 117.2, 111.1, 109.5, 19.8.

6-[5-(4-Carbamimidoylbenzyl)-furan-2-yl]-nicotinamidine acetate salt (38). To a solution of 37 (170 mg, mmol) in glacial acetic acid (8 mL), and ethanol (10 mL) was added 10% palladium on carbon (70 mg). The mixture was placed on Parr hydrogenation apparatus at 50 psi for 4 h at room temperature. The mixture was filtered off through HYFLO. The filtrate was evaporated under reduced pressure and the precipitate was collected and washed with ether to give 38 in 60% yield, mp 213–216° C.$^{dec}$. $^1$H nmr (DMSO-d$_6$); δ 1.78 (s, 6H), 6.43 (d, J=3.3 Hz, 1H), 7.23 (d, J=3.3 Hz, 1H), 7.43 (d, J=7.8 Hz, 2H), 7.49–7.73 (m, 3H), 8.17 (d, J=7.8 Hz, 1H), 8.89 (s, 1H). Calcd. for C$_{18}$H$_{17}$N$_5$O·2AcOH·3H$_2$O·0.35EtOH: C, 53.50; H, 6.54; N, 13.74. Found C, 53.57; H, 6.51; N, 13.37.

Example 8

Table 1 shows potent in vitro data for the compounds of Examples 1–7. Two compounds (7, 20) show IC-50 values versus *Trypanosoma brucei rhodesiense* (T.b.r.) at less than 10 ng/ml. Four compounds (7, 4, 5, 27) show IC-50 values versus *Plasmodium falciparum* (p.f.) at less than 10 ng/ml. L-6 cells were also tested for cytotoxicity. Compound 7 and its prodrug 5 cure the virulent STIB900 strain of T. b. r. in a mouse model. In an experiment slated for 180 days, the prodrug 5 yielded parasite free mice in the CNS model through day 120. Thus, compound 5 can be employed as an oral treatment of 2nd stage human African trypanosomiasis.

TABLE 1

In vitro Anti-protozoan Data

| Code | A | B | Y | Z | X | R$^3$, R$^6$ | R$^1$ | T. b. r. IC50 nM | P. f. IC50 NM | L. d. IC50 μM |
|---|---|---|---|---|---|---|---|---|---|---|
|  | CH | CH | CH | CH | O | H | H | 4.5 | 15.5 | 23.3 |
| 7 | N | CH | CH | CH | O | H | H | 7.0 | 6.5 | 101 |
| 4 | N | CH | CH | CH | O | OH | H | 120 | 4.3 | >195 |
| 5 | N | CH | CH | CH | O | OMe | H | 37.1 | 4.9 | 113.3 |
|  | N | CH | CH | CH | O | OEt | H | 8,400 | 7,300 |  |
|  | N | CH | CH | CH | O | H$^{a)}$ | H | 40.7 | 8.8 |  |
|  | N | CH | CH | CH | O | OH$^{b)}$ | H | 13,300 | 41,500 |  |
| 31 | N | CH | CH | CH | O | H | Me |  |  |  |
| 29 | N | CH | CH | CH | O | OH | Me |  |  |  |
|  | N | CH | CH | CH | O | OMe | Me |  |  |  |
| 13 | N | CH | CH | CH | S | H | H |  |  |  |
| 11 | N | CH | CH | CH | S | OH | H | >187,000 | >10,400 | >187,000 |
| 12 | N | CH | CH | CH | S | OMe | H | 9,425 | 133 | 4,891 |
| 20 | CH | N | CH | CH | O | H | H | 3.1 | 18.3 | 47 |
| 17 | CH | N | CH | CH | O | OH | H | 200,000 | >11,700 |  |
| 18 | CH | N | CH | CH | O | OMe | H | 6,500 | 8,500 |  |
| 24 | N | CH | N | CH | O | H | H | 21 | 83 | 193 |
| 22 | N | CH | N | CH | O | OH | H | 55.8 | >10.2 | 77 |

TABLE 1-continued

In vitro Anti-protozoan Data

[Structure shown]

| Code | A | B | Y | Z | X | R³, R⁶ | R¹ | T. b. r. IC50 nM | P. f. IC50 NM | L. d. IC50 μM |
|---|---|---|---|---|---|---|---|---|---|---|
| 27 | N | CH | N | CH | O | OMe | H | 11.1 | 1.77 | >166 |
| | CH | N | CH | N | O | H | H | 7.0 | 3.9 | |
| | CH | N | CH | N | O | OH | H | >21,000 | >10,500 | |
| | CH | N | CH | N | O | OMe | H | 1,910 | 1,310 | | a) amidine in Y–Z ring is meta;
b) amidoxime in Y–Z ring is meta;

It will be understood that various details of the invention can be changed without departing from the scope of the invention. Furthermore, the foregoing description is for the purpose of illustration only, and not for the purpose of limitation—the invention being defined by the claims appended hereto.

What is claimed is:

1. A compound of Formula (I):

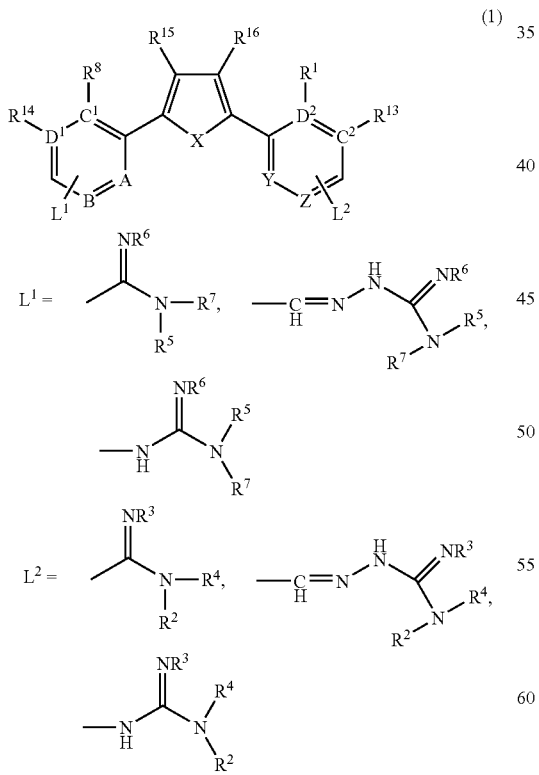

wherein:
X is selected from the group consisting of O, S, and NR¹⁷, where R¹⁷ is hydrogen or lower alkyl;

A and Y are CH, N, NR¹⁷, O, or S;

C¹ and C² are each C or N, wherein C¹ and C² are the same or different;

D¹ and D² are each C or N, wherein D¹ and D² are the same or different;

B and Z are CH, N, or NR¹⁷, provided that B, Z, or both B and Z are not present when A, Y, or both A and Y are O, S, or NR¹⁷;

R¹³, R¹⁴, R¹ and R⁸ can be present or absent, and when present are selected from the group consisting of H, lower alkyl, halogen, alkoxyl, aryloxyl, aralkoxy and hydroxyl;

R¹⁵ and R¹⁶ are selected from the group consisting of H, lower alkyl, halogen, aryloxyl, aralkoxy and hydroxyl;

R³ and R⁶ are each independently selected from the group consisting of H, hydroxy, lower alkyl, cycloalkyl, aryl, aralkyl, alkoxyl, hydroxycycloalkyl, alkoxycycloalkyl, hydroxyalkyl, aminoalkyl, acyloxy, acetoxy, and alkylaminoalkyl; and R², R⁴, R⁵ and R⁷ are each independently selected from the group consisting of H, lower alkyl, alkoxyalkyl, cycloalkyl, aryl, aralkyl, hydroxyalkyl, aminoalkyl, and alkylaminoalkyl, or R² and R⁴ together or R⁵ and R⁷ together represent a C₂ to C₁₀ alkyl, hydroxyalkyl, or alkylene, or R³ and R⁴ together or R⁶ and R⁷ together are:

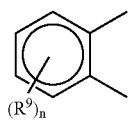

wherein n is a number from 1 to 3, and R⁹ is H or —CONHR¹⁰NR¹¹R¹², wherein R¹⁰ is lower alkyl and R¹¹ and R¹² are each independently selected from the group consisting of H and lower alkyl; and wherein at least one A, B, Y, and Z are selected from the group consisting of N, NR¹⁷, O, and S.

2. A compound of Formula (I):

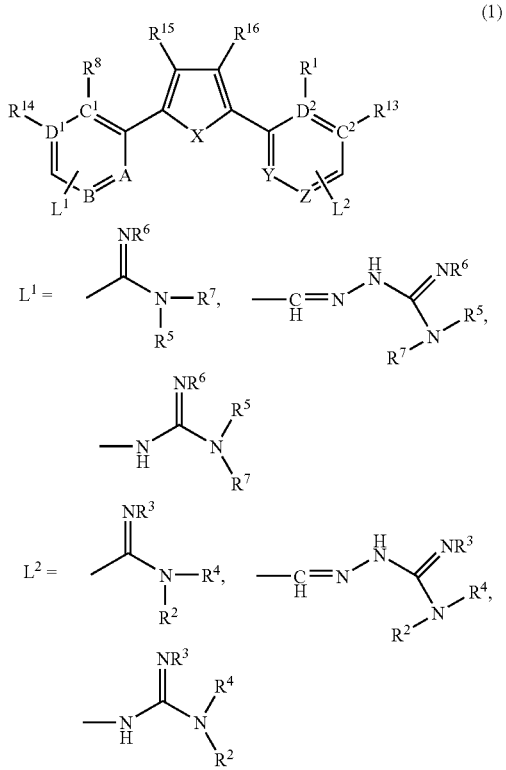

(1)

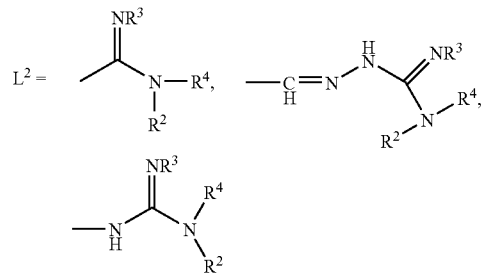

wherein A and B are different and N or CH; Y and Z are CH; X is O or S; $R^2$, $R^4$, $R^5$, and $R^7$ are each H; $R^3$ and $R^6$ are selected from the group consisting of H, OH, methyl, methoxy, and acetoxy; $R^1$ and $R^8$ can be present or absent and when present are selected from the group consisting of H, OH, methyl, methoxy, and acetoxy; $R^{13}$ and $R^{14}$ can be present or absent and when present are selected from the group consisting of H, lower alkyl, halogen, alkoxy, aryloxyl, aralkoxy and hydroxyl; $R^{15}$ and $R^{16}$ are selected from the group consisting of H, lower alkyl, halogen, aryloxyl, aralkoxy and hydroxyl; and $C^1$, $C^2$, and $D^2$ are each C or N.

3. A compound of Formula (I):

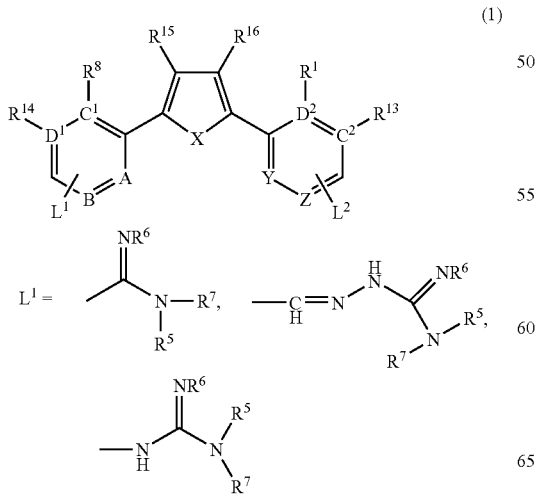

(1)

wherein A and B are CH; X is O; Y is O; Z is not present; $R^2$, $R^4$, $R^5$, and $R^7$ are each H; $R^3$ and $R^6$ are selected from the group consisting of H, OH, methyl, methoxy, and acetoxy; $R^1$ and $R^8$ can be present or absent and when present are selected from the group consisting of H, OH, methyl, methoxy, and acetoxy; $R^{13}$ and $R^{14}$ can be present or absent and when present are selected from the group consisting of H, lower alkyl, halogen, alkoxy, aryloxyl, aralkoxy and hydroxyl; $R^{15}$ and $R^{16}$ are selected from the group consisting of H, lower alkyl, halogen, aryloxyl, aralkoxy and hydroxyl; and $C^1$, $C^2$, $D^1$, and $D^2$ are each C or N.

4. The compound of claim 1, further comprising a pharmaceutically acceptable carrier.

5. The compound of claim 2, wherein A is N; B is CH; X is O; $R_1$ and $R_8$ are H; $R_3$ and $R_6$ are methoxy; and the compound has the structure:

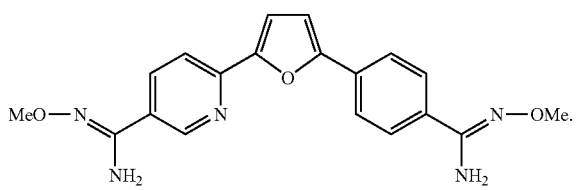

6. A method of treating a microbial infection in a subject in need thereof, the method comprising administering to the subject an effective amount of a compound of Formula (I):

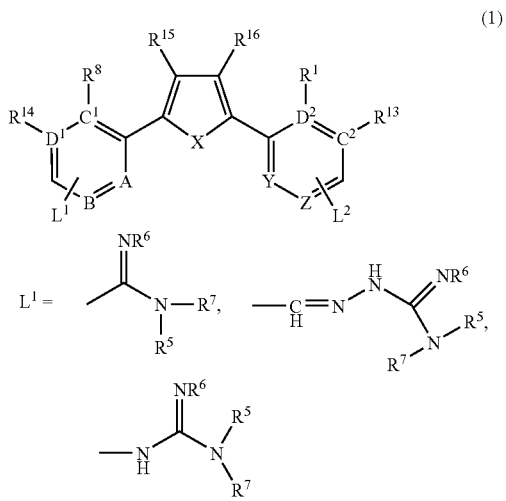

(1)

-continued

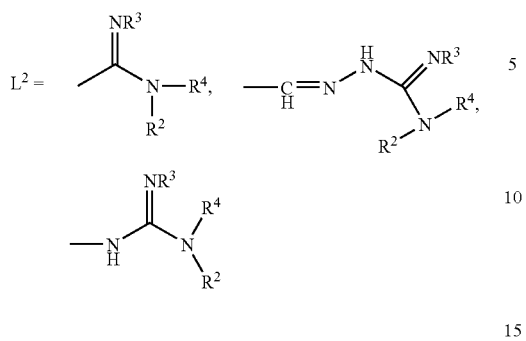

wherein:
X is selected from the group consisting of O, S, and NR$^{17}$, where R$^{17}$ is hydrogen or lower alkyl;
A and Y are CH, N, NR$^{17}$, O, or S;
C$^1$ and C$^2$ are each C or N, wherein C$^1$ and C$^2$ are the same or different;
D$^1$ and D$^2$ are each C or N, wherein D$^1$ and D$^2$ are the same or different;
B and Z are CH, N or NR$^{17}$, provided that B, Z, or both B and Z are not present when A, Y, or both A and Y are O, S, or NR$^{17}$;
R$^{13}$, R$^{14}$, R$^1$ and R$^8$ can be present or absent, and when present are selected from the group consisting of H, lower alkyl, halogen, alkoxyl, aryloxyl, aralkoxy and hydroxyl;
R$^{15}$ and R$^{16}$ are selected from the group consisting of H, lower alkyl, halogen, alkoxyl, aryloxyl, aralkoxy and hydroxyl;
R$^3$ and R$^6$ are each independently selected from the group consisting of H, hydroxy, lower alkyl, cycloalkyl, aryl, aralkyl, alkoxyl, hydroxycycloalkyl, alkoxycycloalkyl, hydroxyalkyl, aminoalkyl, acyloxy, acetoxy, and alkylaminoalkyl; and R$^2$, R$^4$, R$^5$ and R$^7$ are each independently selected from the group consisting of H, lower alkyl, alkoxyalkyl, cycloalkyl, aryl, aralkyl, hydroxyalkyl, aminoalkyl, and alkylaminoalkyl, or R$^2$ and R$^4$ together or R$^5$ and R$^7$ together represent a C$_2$ to C$_{10}$ alkyl, hydroxyalkyl, or alkylene, or R$^3$ and R$^4$ together or R$^6$ and R$^7$ together are:

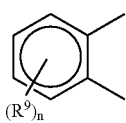

wherein n is a number from 1 to 3, and R$^9$ is H or —CONHR$^{10}$NR$^{11}$R$^{12}$, wherein R$^{10}$ is lower alkyl and R$^{11}$ and R$^{12}$ are each independently selected from the group consisting of H and lower alkyl; and
wherein at least one A, B, Y, and Z are selected from group consisting of N, NR$^{17}$, O, and S.

7. A method of treating a microbial infection in a subject in need thereof, the method comprising administering to the subject an effective amount of a compound of Formula (I):

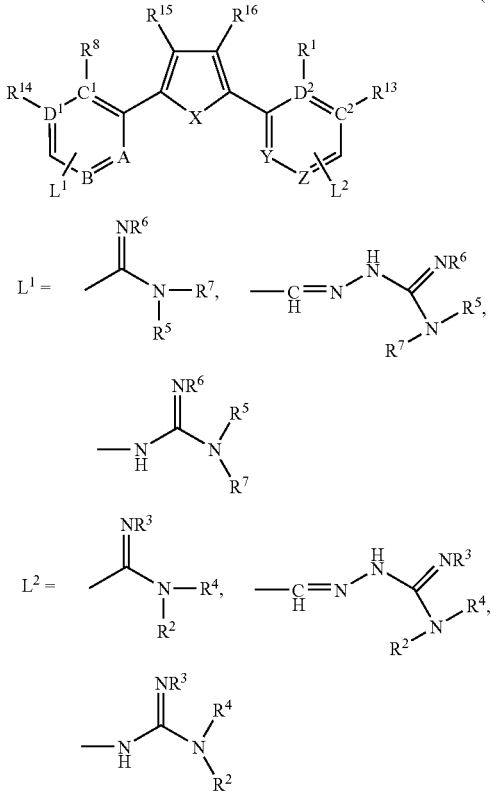

wherein A and B are different and N or CH; Y and Z are CH; X is O or S; R$^2$, R$^4$, R$^5$, R$^7$ are each H; R$^3$ and R$^6$, are selected from the group consisting of H, OH, methyl, methoxy, and acetoxy; R$^1$ and R$^8$ can be present or absent and when present are selected from the group consisting of H, OH, methyl, methoxy, and acetoxy; R$^{13}$ and R$^{14}$ can be present or absent and when present are selected from the group consisting of H, lower alkyl, halogen, alkoxy, aryloxyl, aralkoxy and hydroxyl; R$^{15}$ and R$^{16}$ are selected from the group consisting of H, lower alkyl, halogen, alkoxy, aryloxyl, aralkoxy and hydroxyl; and C$^1$, C$^2$, and D$^2$ are each C or N.

8. A method of treating a microbial infection in a subject in need thereof, the method comprising administering to the subject an effective amount of a compound of Formula (I):

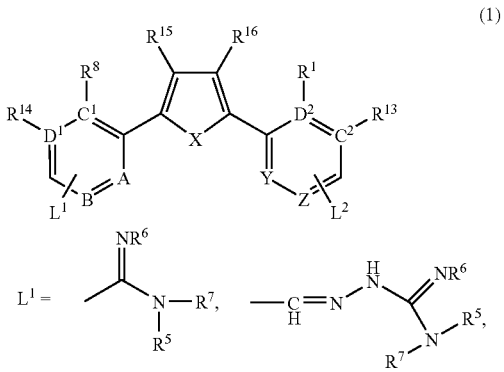

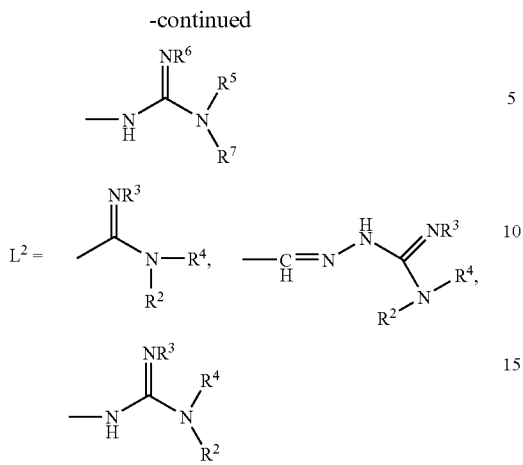

wherein A and B are CH; X is O; Y is O; Z is not present; $R^2$, $R^4$, $R^5$, and $R^7$ are each H; $R^3$ and $R^6$ are selected from the group consisting of H, OH, methyl, methoxy, and acetoxy; $R^1$ and $R^8$ can be present or absent and when present are selected from the group consisting of H, OH, methyl, methoxy, and acetoxy; $R^{13}$ and $R^{14}$ can be present or absent and when present are selected from the group consisting of H, lower alkyl, halogen, alkoxy, aryloxyl, aralkoxy and hydroxyl; $R^{15}$ and $R^{16}$ are selected from the group consisting of H, lower alkyl, halogen, aryloxyl, aralkoxy and hydroxyl; and $C^1$, $C^2$, $D^1$, and $D^2$ are each C or N.

9. The method of claim 6, wherein the microbial infection is a *Trypanosoma brucei rhodesiense* infection or a *Plasmodium falciparum* infection.

10. The method of claim 7, wherein A is N; B is CH; X is O; $R_1$ and $R_8$ are H; $R_3$ and $R_6$ are methoxy; and the compound has the structure:

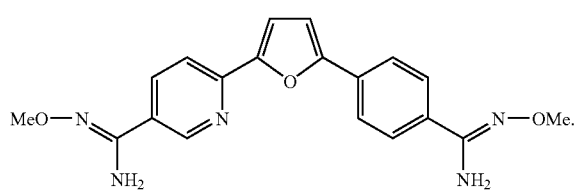

11. The method of claim 10, wherein the microbial infection is a *Trypanosoma brucei rhodesiense* infection or a *Plasmodium falciparum* infection.

12. A pharmaceutical formulation comprising:
(a) a compound of Formula (I):

(1)

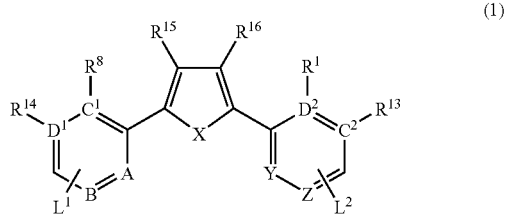

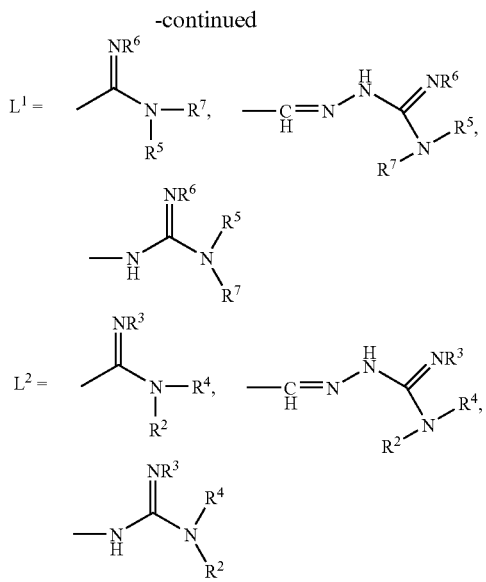

wherein:
X is selected from the group consisting of O, S, and $NR^{17}$, where $R^{17}$ is hydrogen or lower alkyl;
A and Y are CH, N, $NR^{17}$, O, or S;
$C^1$ and $C^2$ are each C or N, wherein $C^1$ and $C^2$ are the same or different;
$D^1$ and $D^2$ are each C or N, wherein $D^1$ and $D^2$ are the same or different;
B and Z are CH, N or $NR^{17}$, provided that B, Z, or both B and Z are not present when A, Y, or both A and Y are O, S, or $NR^{17}$;
$R^{13}$, $R^{14}$, $R^1$ and $R^8$ can be present or absent, and when present are selected from the group consisting of H, lower alkyl, halogen, alkoxyl, aryloxyl, aralkoxy and hydroxyl;
$R^{15}$ and $R^{16}$ are selected from the group consisting of H, lower alkyl, halogen, alkoxyl, aryloxyl, aralkoxy and hydroxyl;
$R^3$ and $R^6$ are each independently selected from the group consisting of H, hydroxy, lower alkyl, cycloalkyl, aryl, aralkyl, alkoxyl, hydroxycycloalkyl, alkoxycycloalkyl, hydroxyalkyl, aminoalkyl, acyloxy, acetoxy, and alkylaminoalkyl; and $R^2$, $R^4$, $R^5$ and $R^7$ are each independently selected from the group consisting of H, lower alkyl, alkoxyalkyl, cycloalkyl, aryl, aralkyl, hydroxyalkyl, aminoalkyl, and alkylaminoalkyl, or $R^2$ and $R^4$ together or $R^5$ and $R^7$ together represent a $C_2$ to $C_{10}$ alkyl, hydroxyalkyl, or alkylene, or $R^3$ and $R^4$ together or $R^6$ and $R^7$ together are:

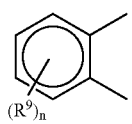

wherein n is a number from 1 to 3, and $R^9$ is H or —$CONHR^{10}NR^{11}R^{12}$, wherein $R^{10}$ is lower alkyl and $R^{11}$ and $R^{12}$ are each independently selected from the group consisting of H and lower alkyl; and wherein at least one A, B, Y, and Z are selected from group consisting of N, $NR^{17}$, O, and S; and (b) a pharmaceutically acceptable carrier.

13. A pharmaceutical formulation comprising:
(a) a compound of Formula (I):

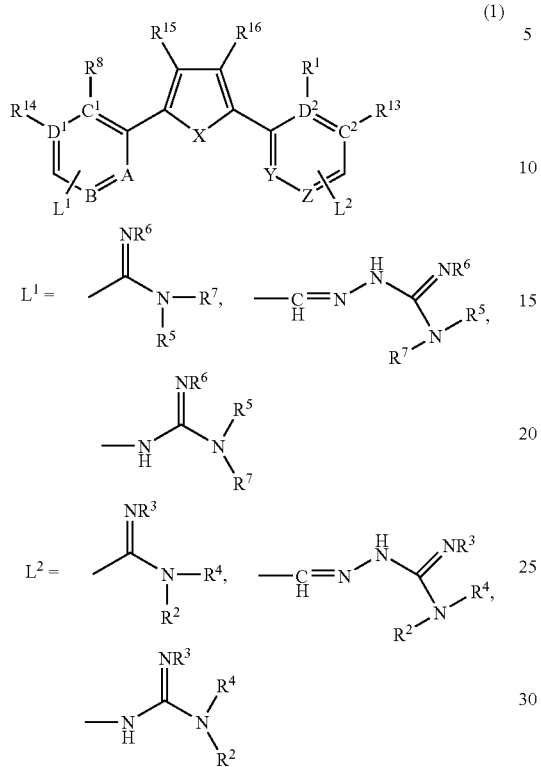

wherein A and B are different and N or CH; Y and Z are CH; X is O or S; $R^2$, $R^4$, $R^5$, $R^7$ are each H; $R^3$ and $R^6$ are selected from the group consisting of H, OH, methyl, methoxy, and acetoxy; $R^1$ and $R^8$ can be present or absent and when present are selected from the group consisting of H, OH, methyl, methoxy, and acetoxy; $R^{13}$ and $R^{14}$ can be present or absent and when present are selected from the group consisting of H, lower alkyl, halogen, alkoxy, aryloxyl, aralkoxy and hydroxyl; $R^{15}$ and $R^{16}$ are selected from the group consisting of H, lower alkyl, halogen, alkoxy, aralkoxy and hydroxyl; and $C^1$, $C^2$, $D^1$, and $D^2$ are each C or N; and (b) a pharmaceutically acceptable carrier.

14. A pharmaceutical formulation comprising:
(a) a compound of Formula (I):

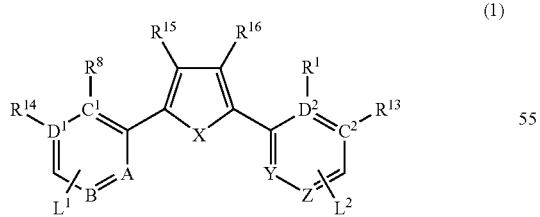

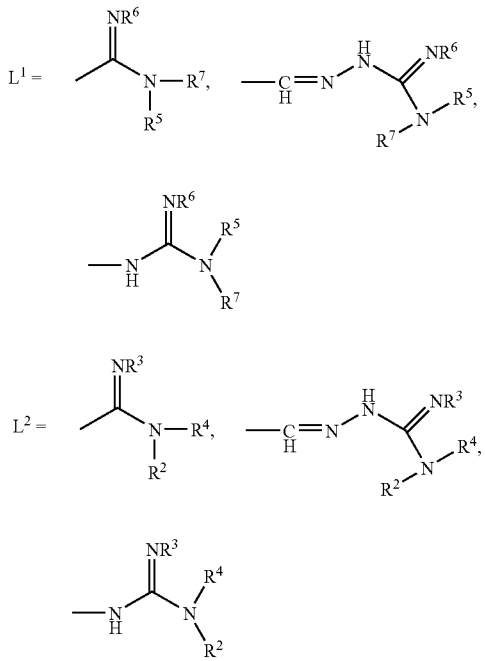

wherein A and B are CH; X is O; Y is O; Z is not present; $R^2$, $R^4$, $R^5$, and $R^7$ are each H; $R^3$ and $R^6$ are selected from the group consisting of H, OH, methyl, methoxy, and acetoxy; $R^1$ and $R^6$ can be present or absent and when present are selected from the group consisting of H, OH, methyl, methoxy, and acetoxy; $R^{13}$ and $R^{14}$ can be present or absent and when present are selected from the group consisting of H, lower alkyl, halogen, alkoxy, aryloxyl, aralkoxy and hydroxyl; $R^{15}$ and $R^{16}$ are selected from the group consisting of H, lower alkyl, halogen, alkoxy, aryloxyl, aralkoxy and hydroxyl; and $C^1$, $C^2$, $D^1$, and $D^2$ are each C or N; and (b) a pharmaceutically acceptable carrier.

15. The pharmaceutical formulation of claim 13, wherein A is N; B is CH; X is O; $R_1$ and $R_8$ are H; $R_3$ and $R_6$ are methoxy; and the compound has the structure:

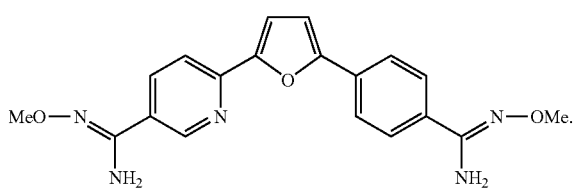

* * * * *